United States Patent
Mowat et al.

(10) Patent No.: US 10,611,645 B2
(45) Date of Patent: *Apr. 7, 2020

(54) ZEOLITE HAVING A ONE-DIMENSIONAL CHANNEL SYSTEM, 10-MEMBERED RINGS AND 12-MEMBERED RINGS

(71) Applicant: UOP LLC, Des Plaines, IL (US)

(72) Inventors: John P. S. Mowat, Arlington Heights, IL (US); Wharton Sinkler, Des Plaines, IL (US); Christopher P. Nicholas, Evanston, IL (US); Mark A. Miller, Niles, IL (US); Melissa M. Galey, Chicago, IL (US)

(*) Notice: Subject to any disclaimer, the term of this patent is extended or adjusted under 35 U.S.C. 154(b) by 22 days.

This patent is subject to a terminal disclaimer.

(21) Appl. No.: 15/658,825

(22) Filed: Jul. 25, 2017

(65) Prior Publication Data

US 2018/0099875 A1    Apr. 12, 2018

Related U.S. Application Data

(60) Provisional application No. 62/405,055, filed on Oct. 6, 2016.

(51) Int. Cl.
*C01B 39/48* (2006.01)
*B01J 29/70* (2006.01)
(Continued)

(52) U.S. Cl.
CPC .............. *C01B 39/48* (2013.01); *B01J 20/10* (2013.01); *B01J 20/18* (2013.01); *B01J 29/70* (2013.01);
(Continued)

(58) Field of Classification Search
CPC ....... C01B 39/46; C01B 39/48; C01B 39/026; B01J 29/70; B01J 20/10; B01J 20/18;
(Continued)

(56) References Cited

U.S. PATENT DOCUMENTS 6,776,975 B2    8/2004 Wilson et al.
8,361,435 B2 *  1/2013 Fecant .................... B01J 20/10
                                          423/706
(Continued)

OTHER PUBLICATIONS

Lobo et al, "SSZ-26 and SSZ-33: Two Molecular Sieves with Intersecting 10- and 12-Ring Pores", Science, vol. 262 pp. 1543-1546 (Dec. 1993).*

(Continued)

*Primary Examiner* — David M Brunsman

(57) ABSTRACT

A new crystalline aluminosilicate zeolite comprising a novel framework has been synthesized that has been designated UZM-55. This zeolite is represented by a three-dimensional framework of at least $SiO_2$ tetrahedral units and an empirical composition in the as-synthesized and anhydrous basis expressed by an empirical formula of:

$$M_m{}^{n+}R_rAl_xE_ySiO_z$$

where M represents a metal or metals from zinc or Group 1 (IUPAC 1), Group 2 (IUPAC 2), Group 3 (IUPAC 3) or the lanthanide series of the periodic table, R is a structure directing agent or agents such as 1,6-bis(N-methylpiperidinium)hexane, and E is an element selected from the group consisting of gallium, iron, boron and mixtures thereof. Catalysts made from UZM-55 have utility in various hydrocarbon conversion reactions including methanol to hydrocarbons (MTH).

14 Claims, 10 Drawing Sheets

(51) Int. Cl.
*C07C 1/20* (2006.01)
*B01J 20/10* (2006.01)
*B01J 20/18* (2006.01)
*C01B 39/00* (2006.01)
*C01B 39/02* (2006.01)
*C07C 2/84* (2006.01)
*B01J 29/86* (2006.01)

(52) U.S. Cl.
CPC ............ *C01B 39/00* (2013.01); *C01B 39/026* (2013.01); *C07C 1/20* (2013.01); *C07C 2/84* (2013.01); *B01J 29/86* (2013.01); *C01P 2002/30* (2013.01); *C01P 2002/72* (2013.01); *C01P 2002/77* (2013.01); *C01P 2004/03* (2013.01); *C01P 2004/04* (2013.01); *C07C 2529/70* (2013.01); *C07C 2529/86* (2013.01); *Y02P 20/52* (2015.11); *Y02P 30/42* (2015.11)

(58) Field of Classification Search
CPC ... B01J 29/86; C01P 2002/72; C01P 2002/77; C07C 1/20; C07C 2/84; C07C 2529/70; C07C 2529/86
See application file for complete search history.

(56) References Cited

U.S. PATENT DOCUMENTS

| | | | |
|---|---|---|---|
| 8,992,885 B2 | 3/2015 | Nicholas et al. | |
| 9,873,614 B2* | 1/2018 | Lai | C01B 39/48 |
| 9,890,051 B2* | 2/2018 | Xie | C01B 39/48 |
| 2012/0022279 A1* | 1/2012 | Cabiac | B01J 29/70 |
| | | | 554/167 |
| 2015/0158020 A1* | 6/2015 | Nicholas | B01J 29/70 |
| | | | 423/704 |

OTHER PUBLICATIONS

Willhammar et al, "Stacking disorders in zeolites and open-frameworks—structure elucidation and analysis by electron crystallography and X-ray diffraction", Z. Kristallogr, (Oct. 2012).*
Rauk, Pyramidal Inversion. Angew. Chem. Int. Ed. Engl., vol. 9 (1970): 400-414.
Guo, On the relationship between unit cells and channel systems in high silica zeolites with the "butterfly" projection, Z. Kristallogr. 2015; 230(5): 301-309.
U.S. Appl. No. 15/658,681, filed Jul. 25, 2017.

* cited by examiner

ZEOLITE HAVING A ONE-DIMENSIONAL CHANNEL SYSTEM, 10-MEMBERED RINGS AND 12-MEMBERED RINGS

CROSS-REFERENCE TO RELATED APPLICATION

This application claims priority from Provisional Application No. 62/405,055 filed Oct. 6, 2016, the contents of which cited application are hereby incorporated by reference in its entirety.

FIELD OF THE INVENTION

This invention relates to a zeolite having a one-dimensional channel system, 10-membered rings and 12-membered rings. Zeolites with this structure include a new aluminosilicate zeolite designated UZM-55. This zeolite is represented by the empirical formula:

where M represents a metal or metals from zinc or Group 1 (IUPAC 1), Group 2 (IUPAC 2), Group 3 (IUPAC 3) or the lanthanide series of the periodic table, R is an organoammonium cation such as 1,6-bis(N-methylpiperidinium) hexane and E is an element selected from the group consisting of gallium, iron, boron and mixtures thereof. UZM-55 has utility in various hydrocarbon conversion reactions such as methanol to hydrocarbons.

BACKGROUND OF THE INVENTION

Zeolites are crystalline aluminosilicate compositions which are microporous and which are formed from corner sharing $AlO_2$ and/or $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

As used herein, zeolites may be referred to by proper name, such as UZM-39, described in U.S. Pat. No. 8,992,885, or by structure type code, such as TUN. These three letter codes indicate atomic connectivity and hence pore size, shape and connectivity for the various known zeolites. The list of these codes may be found in the ATLAS OF ZEOLITE FRAMEWORK TYPES, which is maintained by the International Zeolite Association Structure Commission at http://www.iza-structure.org/databases/. Zeolites are distinguished from each other on the basis of their composition, crystal structure and adsorption properties. One method commonly used in the art to distinguish zeolites is x-ray diffraction. UZM-55 is a zeolite with a heretofore never before described structure.

Fecant and Bats describe in U.S. Pat. No. 8,361,435 the synthesis of a product they call IZM-2 from the crystallization of a gel comprising at least one organic species R containing two quaternary nitrogen atoms with a particular XRD pattern and having a $SiO_2/Al_2O_3$ ratio preferably in the range from 60 to 600. The present invention involves a particular XRD pattern and has a $SiO_2/Al_2O_3$ ratio of greater than 75, preferably greater than 100 and most preferably greater than 150.

SUMMARY OF THE INVENTION

A new zeolitic material, UZM-55, has been made with a novel framework structure and which has utility in hydrocarbon processes. The present invention relates to zeolite UZM-55, the process of making it and its use as a catalyst in hydrocarbon conversion processes. Accordingly, one embodiment of the invention is a microporous crystalline zeolite having a three-dimensional framework of at least $SiO_2$ tetrahedral units and an empirical composition in the as synthesized and anhydrous basis expressed by an empirical formula of:

where M represents hydrogen or a metal or metals from zinc or Group 1 (IUPAC 1), Group 2 (IUPAC 2), Group 3 (IUPAC 3) or the lanthanide series of the periodic table, "m" is the mole ratio of M to Si and varies from 0 to about 1.0 and is usually close to zero, "n" is the weighted average valence of M and has a value of about 1 to about 3, R is a structure directing agent or agents such as 1,6-bis(N-methylpiperidinium)hexane, "r" is the mole ratio of N from the organic structure directing agent or agents to Si and has a value of about 0 to about 1.0, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation: z=(4+m+3●x+3●y)/2. UZM-55 may exist as unmodified zeolite UZM-55 or as UZM-55 modified zeolite. The UZM-55 containing catalyst may take one of several forms, including for example, a spherical oil-dropped catalyst or an extruded catalyst.

An embodiment of the invention is the structure of UZM-55. The structure of UZM-55 has been solved using x-ray and electron diffraction data. The pore structure of UZM-55 is one-dimensional, where the pore contains both 10-membered and 12-membered rings. The pore is delimited by both 10-membered and 12-membered rings.

Yet another embodiment of the invention is a hydrocarbon conversion process using the zeolite of the present invention. The process comprises contacting a hydrocarbon stream with the zeolite at conversion conditions to give a converted hydrocarbon product. The hydrocarbon conversion processes include methanol to olefins, ethylene to propylene, oligomerization, isomerization of paraffins, paraffin cracking, aromatic conversions such as xylene isomerization, toluene disproportionation, ring opening and cracking to remove benzene co-boilers and alkylation of aromatics with paraffins.

DETAILED DESCRIPTION OF THE INVENTION

Figure 1:
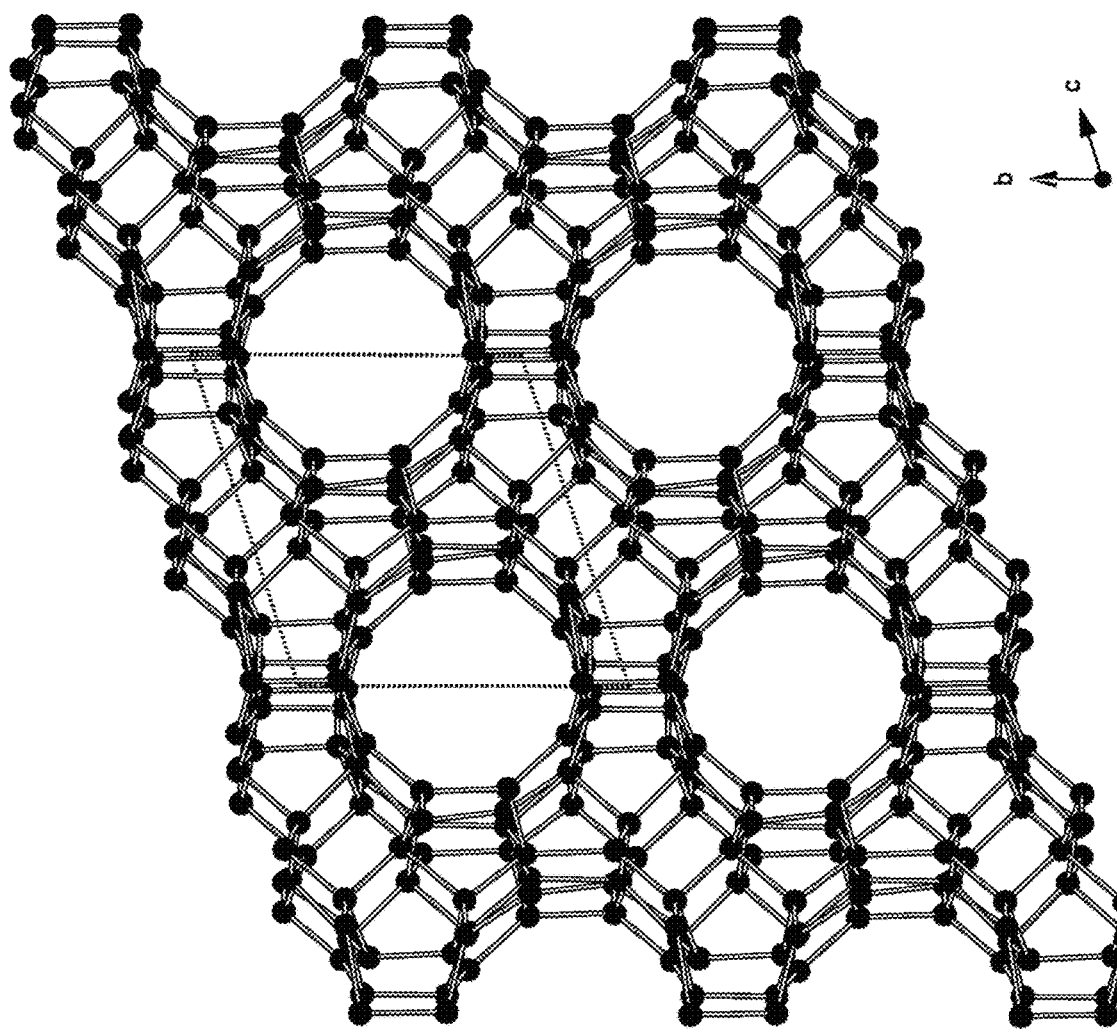
FIG. 1 shows the UZM-55 zeolite structure as a ball and stick model. Black balls are T-sites and the dashed box indicates the outline of the unit cell.

Applicants have prepared an aluminosilicate zeolite whose topological structure is novel and not described in ATLAS OF ZEOLITE FRAMEWORK TYPES, which is maintained by the International Zeolite Association Structure Commission at http://www.iza-structure.org/databases/. This new zeolite has been designated as UZM-55. As will be shown in detail, UZM-55 is different from the known zeolites in a number of its characteristics, has a novel pore topology comprising 10-membered rings and 12-membered rings in the same pore, and finds utility as a catalyst in hydrocarbon conversion processes. Zeolites may be distinguished from each other on the basis of their composition, crystal structure and adsorption properties. Channel systems for known zeolites are described in the Atlas of Zeolite Framework Types as having zero-dimensional, one-dimensional, two-dimensional or three-dimensional pore systems. A zero-dimensional pore system has no pore system running through the zeolite crystal, instead only possessing internal cages. A one-dimensional pore system contains a pore delimited by 8-membered rings or larger that run substantially down a single axis of a crystal. MTW is a known one-dimensional zeolite comprising a pore delimited by 12-membered rings running down the b axis. Two-dimensional pore (channel) containing zeolites contain intersecting pores that extend through two-dimensions of a zeolite crystal, but travel from one side of the third dimension of the zeolite crystal to the other side of the third dimension is not possible, while zeolites containing three-dimensional channel systems have a system of pores intersecting, often in a mutually orthogonal manner, such that travel from any side of a zeolite crystal to another is possible.

UZM-55 is represented in the as synthesized and anhydrous basis by the empirical formula:

where M represents hydrogen or a metal or metals from zinc or Group 1 (IUPAC 1), Group 2 (IUPAC 2), Group 3 (IUPAC 3) or the lanthanide series of the periodic table, "m" is the mole ratio of M to Si and varies from 0 to about 1.0 and is usually close to zero, "n" is the weighted average valence of M and has a value of about 1 to about 3, R is a structure directing agent or agents such as 1,6-bis(N-methylpiperidinium)hexane, "r" is the mole ratio of N from the organic structure directing agent or agents to Si and has a value of about 0 to about 1.0, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation: z=(4+m+3●x+3●y)/2. Specific examples of M include but are not limited to lithium, potassium, rubidium, cesium, magnesium, calcium, strontium, barium, zinc, yttrium, lanthanum, gadolinium, and mixtures thereof. UZM-55 is characterized in that it has an x-ray diffraction pattern having at least the d-spacings and intensities set forth in Table 1.

In an embodiment, "x" may be less than 0.026 or may be less than 0.02 or may be less than 0.0133 or less than 0.003. In an embodiment, "y" may be less than 0.026 or may be less than 0.02 or may be less than 0.0133 or less than 0.003. In an embodiment, m is 0. In an embodiment, m is less than 0.05 or less than 0.1. In an embodiment, "r" has a value of from about 0.005 to about 0.08 or has a value of from about 0.01 to about 0.06.

We disclosed a process for preparing a pre-reacted aqueous solution of substituted hydrocarbons and amines incapable of undergoing pyramidal inversion, which overcomes typical difficulties to yield the structure directing agent or agents R, now published as US2015/0158020, herein incorporated by reference. Other methods of synthesizing R may be utilizable. The inventors made the surprising discovery that a substituted hydrocarbon and amine may be reacted in an aqueous solution at (or slightly above) room temperature (20° C.-80° C.) to yield an aqueous solution comprising the OSDA (organic structure directing agent). This solution may then be used without purification in the synthesis of zeolites. This procedure thereby allows the preparation of SDAs, such as unusual quaternary ammonium salts, from readily available starting reagents in a facile and practical manner.

The IUPAC definition of pyramidal inversion is given as, "a polytopal rearrangement in which the change in bond directions to a three-coordinate central atom having a pyramidal arrangement of bonds (tripodal arrangement) causes the central atom (apex of the pyramid) to appear to move to an equivalent position on the other side of the base of the pyramid. If the three ligands to the central atom are different pyramidal inversion interconverts enantiomers." The tripodal nature of many nitrogen compounds result in the ability of these compounds to undergo pyramidal inversion. Typically, the energy barrier to inversion is low for unconstrained molecules. For example, ammonia ($NH_3$) has an inversion barrier of 24.5 kJ $mol^{-1}$, with an observed inversion frequency of about $2.4*10^{10}$ $s^{-1}$, dimethylamine has an inversion barrier of 18 kJ $mol^{-1}$, triisopropylamine has an inversion barrier of 6-8 kJ $mol^{-1}$ and dimethylethylamine has an inversion barrier of 22 kJ $mol^1$. However, inversion barrier energy can become very high when the nitrogen substituents are part of a small ring or other rigid molecule as in the case of 1-methylpyrrolidine. Molecules defined as essentially incapable of undergoing pyramidal inversion have an inversion barrier energy of at least about 28 kJ mol$^{-1}$ and more preferably of at least about 30 kJ mol$^{-1}$. A discussion of pyramidal inversion may be found in Rauk, A., et al., (1970), Pyramidal Inversion. ANGEW. CHEM. INT. ED. ENGL., 9: 400-414, with further discussion specifically for amines found in INORGANIC CHEMISTRY edited by Arnold F. Holleman, et al., Academic Press, 2001. Molecules may exist in many conformers or folding patterns. For example, it is well known that both chair and boat forms of cyclohexane exist and interconvert between the two different conformers. In an aspect of the invention, at least one conformer of the amine is essentially incapable of undergoing pyramidal inversion.

Organoammonium OSDAs prepared by the methods presented here are in aqueous solution and do not pose odor and flashpoint concerns. In an aspect, the invention provides a method for synthesizing an organoammonium compound. The method includes the steps of: preparing an aqueous mixture comprising water, a substituted hydrocarbon and an amine other than trimethylamine wherein the amine is a tertiary or secondary amine having 9 or less carbon atoms and being essentially incapable of undergoing pyramidal inversion, or combinations thereof; reacting the aqueous mixture; obtaining a solution comprising the organoammonium compound; and wherein the mixture and the solution are essentially free of aluminum and silicon. In one version of the method, the step of reacting the aqueous mixture occurs at a temperature from about 20° C. to about 100° C., and for a time from about 0.5 hours to about 48 hours. In another version of the method, the organoammonium product is used as a structure directing agent in the synthesis of UZM-55.

In another version of the method for synthesizing the organoammonium compound, the substituted hydrocarbon is selected from the group consisting of halogen substituted alkanes having from 2 to 8 carbon atoms, α,ω-dihalogen substituted alkanes having from 3 to 6 carbon atoms, di-halogen substituted alkanes having from 3 to 8 carbon atoms, tri-halogen substituted alkanes having from 3 to 8 carbons and combinations thereof. In another version of the method, the substituted hydrocarbon is α,ω-dihalogen substituted alkane. In another version of the method, the α,ω-dihalogen substituted alkane is selected from the group consisting of selected from the group consisting of 1,3-dichloropropane, 1,4-dichlorobutane, 1,5-dichloropentane, 1,6-dichlorohexane, 1,3-dibromopropane, 1,4-dibromobutane, 1,5-dibromopentane, 1,6-dibromohexane, 1,3-diiodopropane, 1,4-diiodobutane, 1,5-diiodopentane, 1,6-diiodohexane and combinations thereof. In another version of the method, the α,ω-dihalogen substituted alkane is selected from the group consisting of selected from the group consisting of 1,6-dichlorohexane, 1,6-dibromohexane, and 1,6-diiodohexane.

In another version of the method, the tertiary amine having 9 or fewer carbon atoms and being essentially incapable of undergoing pyramidal inversion is selected from the group consisting of 1-alkylpyrrolidines, 1-alkylpiperidines, 4-alkylmorpholines, 1-methylpiperidine, 1-ethylpyrrolidine, 1-methylpyrrolidine, and combinations thereof. The tertiary amine may be 1-methylpiperidine.

In a version of the method, the structure directing agent or agents R may have the structure of Formula 1: [bis-N,N'-diR$_1$-(piperidinium)-R$_2$]$^{2+}$2X$^-$, wherein R$_1$ is selected from H or an alkyl group having the formula C$_q$H$_{2q+i}$, where q is in the range from 1 to 4, X is halide or hydroxide, the total number of C atoms in the molecule is in the range from 11 to 24, and R$_2$ is an alkyl group having the formula C$_p$H$_{2p}$, where p is in the range from 3 to 8 and is connected to the 1 and 1' N atoms at positions s and t of the alkyl chain where s and t are independently selected from 1 to p. In an embodiment, p may be greater than 5 or equal to 5 or equal to 6. In an embodiment, q may be 1 or q may be 2. In an embodiment, X may be hydroxide. The organoammonium compound R may be 1,6-bis(N-methylpiperidinium)hexane.

The UZM-55 material is made from a reaction mixture having a composition expressed in terms of mole ratios of the oxides of:

where M represents a metal or metals from hydrogen, zinc or Group 1 (IUPAC 1), Group 2 (IUPAC 2), Group 3 (IUPAC 3) or the lanthanide series of the periodic table, "a" has a value from 0 to about 0.5, R is an organic structure directing agent or agents, "b" has a value from about 0 to about 0.3, "c" has a value of from 0.0 to about 0.015, E is an element selected from the group consisting of gallium, iron, boron and mixtures thereof, "e" has a value from 0.0 to about 0.015, and "g" has a value from about 20 to about 40. The process may further comprise adding UZM-55 seeds to the reaction mixture. Sources of M include but are not limited to sodium hydroxide, potassium hydroxide, sodium aluminate, potassium aluminate, sodium silicate, and potassium silicate. In an embodiment, "a" may be less than 0.3 or less than 0.1. In an embodiment, "b" may be less than 0.25 or less than 0.2 or less than 0.15 or may be greater than 0.05 or greater than 0.1. The source of E is selected from the group consisting of alkali borates, boric acid, precipitated gallium oxyhydroxide, gallium sulfate, ferric sulfate, ferric chloride and mixtures thereof. The sources of aluminum include but are not limited to aluminum alkoxides, precipitated aluminas, aluminum metal, aluminum hydroxide, sodium aluminate, potassium aluminate, aluminum salts and alumina sols. Specific examples of aluminum alkoxides include, but are not limited to aluminum sec-butoxide and aluminum ortho isopropoxide. In an embodiment, "c" may be less than 0.01 or less than 0.008 or less than 0.005 or less than 0.0017. Sources of silica include but are not limited to tetraethylorthosilicate, colloidal silica, fumed silica, precipitated silica and alkali silicates. In an embodiment, "g" may be greater than 25 or greater than 27 or may be less than 35 or less than 30.

The reaction mixture is reacted at a temperature of about 150° to about 185° C. for a time of about 1 day to about 3 weeks in a stirred, sealed reaction vessel under autogenous pressure. After crystallization is complete, the solid product is isolated from the heterogeneous mixture by means such as filtration or centrifugation, and may be washed with deionized water and dried in air at ambient temperature at about 100° C. The reaction mixture may be reacted at a temperature of about 160° to about 175° C. for a time of about 1 day to about 3 weeks. In an embodiment, the reaction mixture is reacted at a temperature of about 160° to about 175° C. for a time of about 1 day to about 1 week.

UZM-55, in the as-synthesized and anhydrous basis, is characterized by the x-ray diffraction pattern, having at least the d-spacings and relative intensities set forth in Table 1 below. Those peaks characteristic of UZM-55 are shown in Table 1. UZM-55 is a material of quite low symmetry, so many peaks may not be a single reflection, but may actually be a combination of reflections. Additional peaks, particularly those of very weak intensity, may also be present. All peaks of medium or higher intensity present in UZM-55 are represented in Table 1. Diffraction patterns herein were obtained using a typical laboratory powder diffractometer, utilizing the $K_\alpha$ line of copper; Cu K alpha. Typical errors in two theta are 0.02. From the position of the diffraction peaks represented by the angle 2θ, the characteristic interplanar distances $d_{hkl}$ of the sample can be calculated using the Bragg equation. The intensity is calculated on the basis of a relative intensity scale attributing a value of 100 to the line representing the strongest peak on the X-ray diffraction pattern, and then: very weak (VW) means less than 15; weak (W) indicates in the range 15 to 30; weak to medium (MW) means in the range 30 to 50; medium (M) means in the range 50 to 65; strong (S) means in the range 65 to 85; very strong (VS) means more than 85. Intensities may also be shown as inclusive ranges of the above. The X-ray diffraction patterns from which the data (d spacing and intensity) are obtained are characterized by a large number of reflections some of which are broad peaks or peaks which form shoulders on peaks of higher intensity. Some or all of the shoulders may not be resolved. This may be the case for samples of low crystallinity, of particular morphological structures or for samples with crystals which are small enough to cause significant broadening of the X-rays. This can also be the case when the equipment or operating conditions used to produce the diffraction pattern differ significantly from those used in the present case.

TABLE 1

| 2θ | d (Å) | I/I₀ % |
|---|---|---|
| 7.16 | 12.34 | VW-W |
| 7.44 | 11.87 | VW-W |
| 8.58 | 10.30 | VW |
| 21.01* | 4.225 | VS |
| 22.07 | 4.024 | VW |
| 22.75 | 3.906 | MW-M |
| 24.19 | 3.676 | VW |
| 26.41 | 3.372 | VW-W |
| 32.73 | 2.734 | VW |
| 36.37 | 2.468 | VW |
| 44.01 | 2.056 | VW |

In particular, the very strong peak at 4.22 Å is a composite peak of at least two peaks as indicated by the asterisk. In an embodiment, the peak at d=4.22 Å is the strongest peak. In an embodiment, only 1 peak of very strong intensity exists. In an embodiment, no more than 2 peaks of greater than 30 intensity exist.

As will be shown in detail in the examples, the UZM-55 material is thermally stable up to a temperature of at least 600° C. and in another embodiment, up to at least 800° C.

In an embodiment, the $SiO_2/Al_2O_3$ ratio of UZM-55 may be greater than 75 or greater than 100 or greater than 150 or greater than 600. In an aspect, UZM-55 is difficult to crystallize at low $SiO_2/Al_2O_3$ ratios. MTW and other competing phases may crystallize in lieu of UZM-55 at $SiO_2/Al_2O_3$ ratios of less than about 80.

As synthesized, the UZM-55 material will contain some exchangeable or charge balancing cations in its pores. These exchangeable cations can be exchanged for other cations, or in the case of organic SDAs, they can be removed by heating under controlled conditions. It may be possible to remove some organic SDAs from the UZM-55 zeolite directly by ion exchange. The UZM-55 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Conditions may be more severe than shown in U.S. Pat. No. 6,776,975. Properties that are modified include porosity, adsorption, Si/Al ratio, acidity, thermal stability, and the like.

After calcination and on an anhydrous basis, the microporous crystalline zeolite UZM-55 has a three-dimensional framework of at least $AlO_2$ and $SiO_2$ tetrahedral units and an empirical composition in the hydrogen form expressed by an empirical formula of $$M_{m'}^{N+}Al_xE_ySiO_z$$

where "m'" is the mole ratio of M to Si and varies from 0 to about 1.0 and is usually close to zero, "N" is the weighted average valence of M and has a value of about +1 to about +3, "X" is the mole ratio of Al to Si and has a value of from 0 to about 0.026, E is an element selected from the group consisting of gallium, iron, boron and mixtures thereof, "Y" is the mole ratio of E to Si and has a value from 0 to about 0.026, and "Z" is the mole ratio of O to (Al+E) and has a value determined by the equation: z=(4+m+3●x+3●y)/2.

In an embodiment, "X" may be less than 0.026 or may be less than 0.02 or may be less than 0.0133 or less than 0.003. In an embodiment, "Y" may be less than 0.026 or may be less than 0.02 or may be less than 0.0133 or less than 0.003. In an embodiment, m' is 0. In an embodiment, m' is less than 0.05 or less than 0.1.

In the calcined form, UZM-55 displays the XRD pattern shown in Table 2. Those peaks characteristic of UZM-55 are shown in Table 2. Additional peaks, particularly those of very weak intensity, may also be present. All peaks of medium or higher intensity present in UZM-55 are represented in Table 2.

TABLE 2

| 2θ | d (Å) | I/I₀ % |
|---|---|---|
| 7.19 | 12.28 | MW-S |
| 7.57 | 11.67 | W-M |
| 8.59 | 10.29 | W-MW |
| 14.72 | 6.013 | VW |
| 21.04* | 4.219 | VS |
| 22.15 | 4.010 | VW |
| 23.03 | 3.859 | MW-M |
| 24.34 | 3.654 | VW |
| 26.63 | 3.345 | VW-W |
| 36.47 | 2.462 | VW |
| 44.49 | 2.035 | VW |

The intensity is calculated on the basis of a relative intensity scale attributing a value of 100 to the line representing the strongest peak on the X-ray diffraction pattern, and relative intensities are described above. In particular, the very strong peak at 4.22 Å is a composite peak of at least two peaks as indicated by the asterisk.

In an embodiment, the peak at d=4.22 Å is the strongest peak. In an embodiment, only the peak at d=4.22 Å is of very strong intensity. In an embodiment, the difference in d space between the first peak of greater than very weak intensity at 12.28 Å and the very strong peak at d=4.22 Å is greater than 7.9 Å or greater than 8.02 Å or greater than 8.04 Å and may be less than 9.0 Å or less than 8.5 Å or less than 8.2 Å. In an embodiment, the absolute value of the difference in 2-theta between the first peak of greater than very weak intensity at 7.19° 2θ and the very strong peak at 21.04° 2θ is less than 13.90 or less than 13.88 and may be greater than 13.6 or greater than 13.7 or greater than 13.8. In an embodiment, the difference in d space between the first peak of greater than very weak intensity at 12.28 Å and the second peak of greater than very weak intensity at d=11.67 Å is greater than 0.50 Å or greater than 0.55 Å or greater than 0.58 Å or greater than 0.60 Å and may be less than 0.70 Å or less than 0.66 Å or less than 0.63 Å. In an embodiment, the absolute value of the difference in 2theta between the first peak of greater than very weak intensity at 7.19° 2θ and the second peak of greater than very weak intensity at 7.57° 2θ is greater than 0.33 or greater than 0.34 Å or greater than 0.36 or greater than 0.37 and may be less than 0.50 or less than 0.45 or less than 0.40.

Also as shown in the examples, as measured by the BET technique using $N_2$ as the adsorbing gas, UZM-55 may have a micropore volume of greater than 0.08 mL/g or greater than 0.10 mL/g or greater than 0.11 mL/g and may have a micropore volume of less than 0.15 mL/g or less than 0.14 mL/g or less than 0.13 mL/g.

Figure 2:
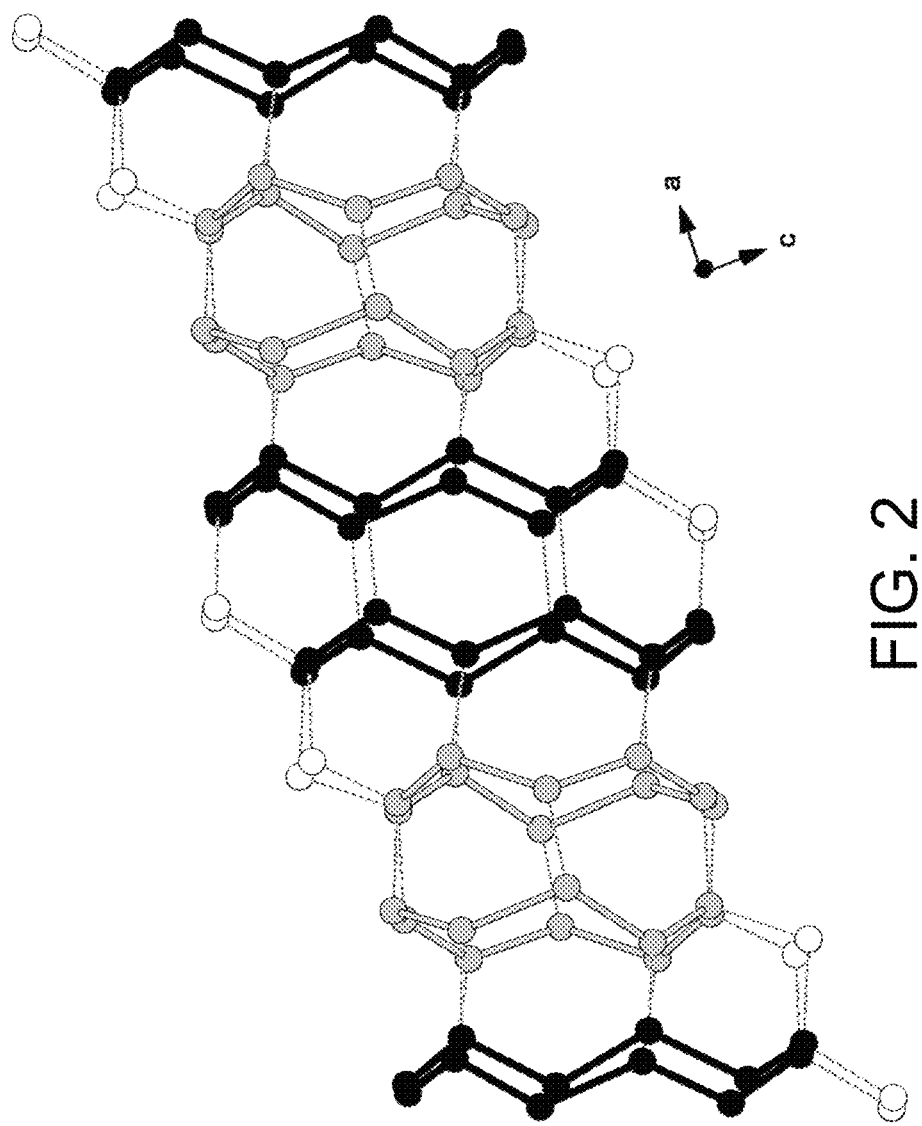
FIG. 2 shows the UZM-55 pore structure perpendicular to the pore. 12-membered rings are indicated in black, 10-membered rings in gray, T-sites not in a ring forming connections between rings in white, and connections between T-sites in dashed lines.

The structure of UZM-55 has been solved using x-ray diffraction, electron diffraction, TEM, model building and Rietveld refinement. Using these techniques, we determined that UZM-55 may possess a unit cell of a=17.80 Å, b=12.23 Å, c=12.93 Å, alpha=71.79°, beta=88.16°, gamma=90.25°. Typical error in the unit cell is ±0.75 Å or about ±0.5 Å on distances and about ±1.0° on angles. The unit cell was proposed from transmission electron diffraction experiments and confirmed by x-ray diffraction. UZM-55 was found to possess a unique triclinic unit cell and t-site connectivity not found in previously described zeolitic materials. Framework models were proposed starting from dislocated MTW frameworks and refined against the x-ray diffraction data. Model building and refinement/optimization methods were then utilized to obtain the final three-dimensionally connected model. UZM-55 is a synthetic porous crystalline material possessing a unique one-dimensional channel system which is defined by 10-membered rings of tetrahedrally coordinated atoms and 12-membered rings of tetrahedrally coordinated atoms. In an aspect, the pore structure is one-dimensional and delimited by both 10-membered rings and 12-membered rings. FIG. 1 shows the UZM-55 zeolite structure as a ball and stick model. Black balls are T-sites and the dashed box indicates the outline of the unit cell. This view is down the a-axis, viewing through the 10-membered and 12-membered ring pore. FIG. 2 shows the UZM-55 pore structure perpendicular to the pore. Here, 12-membered rings are indicated in black, 10-membered rings are indicated in gray, T-sites forming bridging connections between rings are indicated in white, and connections between T-sites are indicated in dashed lines. A 10-membered ring is followed by a 10-membered ring which is followed by a 12-membered ring which is followed by a 12-membered ring before the pattern repeats as one progresses down the pore. Each pair of 10-membered rings is followed by a pair of 12-membered rings which is followed by a pair of 10-membered rings, etc. as one progresses down the one-dimensional pore. Thus, the one-dimensional pore is delimited by both 10-membered rings and 12-membered rings.

Figure 3:
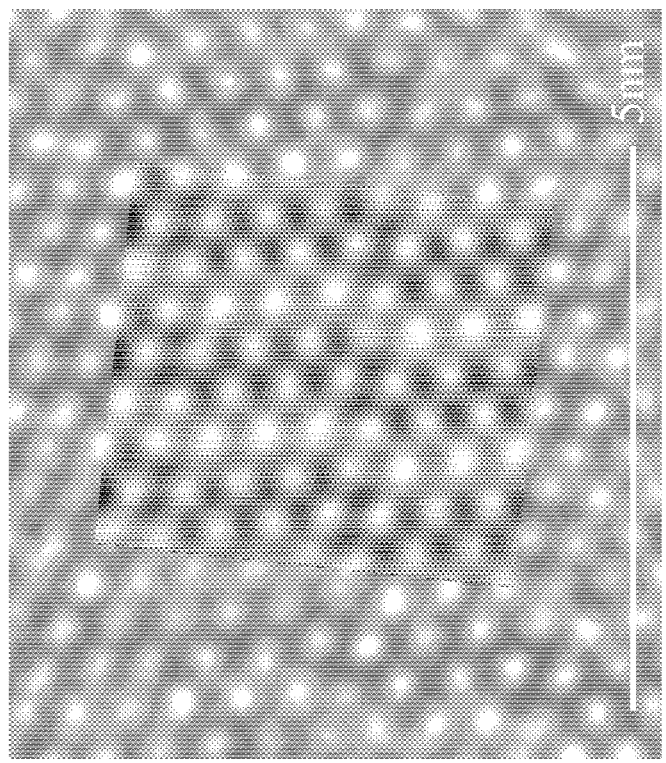
FIG. 3 shows a TEM image of UZM-55 along [0, -1, 0] showing regions of light and dark contrast along with an overlay of the expected contrast generated from the structure solution via a blurred, contrast-inverted projected potential.

FIG. 3 shows an experimental TEM image of UZM-55 along [0, −1, 0] showing regions of light and dark contrast along with an overlay of the expected contrast generated from the structure solution via a blurred, contrast-inverted projected potential. The areas of light contrast undulate through the structure and correspond to the undulation of the 1-dimensional channel running perpendicular to this view. The calculated, expected, TEM image overlaid in FIG. 3 shows the same areas of light and dark contrast as that observed in the experimental image.

The structure of UZM-55 may be defined by its unit cell, the smallest structural unit containing all the structural elements of the material. UZM-55 comprises a framework of tetrahedral atoms (T-atoms) bridged by oxygen atoms, the tetrahedral atom framework defined by the unit cell described above, or less symmetric variants thereof, with atomic coordinates as shown in Table 3 or Table 4, wherein each coordinate position may vary within ±0.75 Å. T-atoms are understood to indicate Si, Al or E atoms. Coordinates in the tables are shown as a fraction of the unit cell, hence site T1 is at a position 16.25 Å, 3.30 Å, 9.63 Å from the origin of the unit cell. Table 3 shows the T-positions of the calcined form of UZM-55 as optimized with the LAMMPS package using the Universal Force Field (UFF) applied via the Scienomics MAPS platform.

TABLE 3

| | Calcined, optimized | | |
|---|---|---|---|
| Site | X | Y | Z |
| T1 | 0.913(3) | 0.270(4) | 0.745(4) |
| T2 | 0.001(3) | 0.121(4) | 0.633(4) |
| T3 | 0.995(3) | 0.512(4) | 0.373(4) |
| T4 | 0.911(3) | 0.129(4) | 0.983(4) |
| T5 | 0.347(3) | 0.135(4) | 0.940(4) |
| T6 | 0.623(3) | 0.208(4) | 0.828(4) |
| T7 | 0.432(3) | 0.507(4) | 0.581(4) |
| T8 | 0.247(3) | 0.697(4) | 0.335(4) |
| T9 | 0.275(3) | 0.466(4) | 0.500(4) |
| T10 | 0.462(3) | 0.278(4) | 0.765(4) |
| T11 | 0.185(3) | 0.223(4) | 0.870(4) |
| T12 | 0.167(3) | 0.456(4) | 0.701(4) |
| T13 | 0.164(3) | 0.094(4) | 0.694(4) |
| T14 | 0.709(3) | 0.175(4) | 0.498(4) |
| T15 | 0.550(3) | 0.239(4) | 0.417(4) |
| T16 | 0.280(3) | 0.212(4) | 0.514(4) |
| T17 | 0.434(3) | 0.141(4) | 0.606(4) |
| T18 | 0.075(3) | 0.106(4) | 0.057(4) |
| T19 | 0.089(3) | 0.103(4) | 0.296(4) |
| T20 | 0.792(3) | 0.143(4) | 0.164(4) |
| T21 | 0.523(3) | 0.103(4) | 0.262(4) |
| T22 | 0.639(3) | 0.109(4) | 0.081(4) |
| T23 | 0.253(3) | 0.070(4) | 0.364(4) |
| T24 | 0.369(3) | 0.038(4) | 0.192(4) |
| T25 | 0.012(3) | 0.742(4) | 0.610(4) |
| T26 | 0.826(3) | 0.286(4) | 0.313(4) |
| T27 | 0.086(3) | 0.729(4) | 0.254(4) |
| T28 | 0.998(3) | 0.879(4) | 0.367(4) |
| T29 | 0.004(3) | 0.487(4) | 0.626(4) |
| T30 | 0.088(3) | 0.870(4) | 0.016(4) |
| T31 | 0.653(3) | 0.864(4) | 0.059(4) |
| T32 | 0.376(3) | 0.791(4) | 0.171(4) |
| T33 | 0.567(3) | 0.492(4) | 0.418(4) |
| T34 | 0.752(3) | 0.302(4) | 0.664(4) |
| T35 | 0.724(3) | 0.534(4) | 0.499(4) |
| T36 | 0.537(3) | 0.721(4) | 0.234(4) |
| T37 | 0.814(3) | 0.776(4) | 0.129(4) |
| T38 | 0.832(3) | 0.543(4) | 0.299(4) |
| T39 | 0.835(3) | 0.905(4) | 0.305(4) |
| T40 | 0.290(3) | 0.824(4) | 0.501(4) |
| T41 | 0.449(3) | 0.760(4) | 0.582(4) |
| T42 | 0.719(3) | 0.787(4) | 0.485(4) |
| T43 | 0.565(3) | 0.858(4) | 0.393(4) |
| T44 | 0.924(3) | 0.893(4) | 0.942(4) |
| T45 | 0.910(3) | 0.896(4) | 0.704(4) |
| T46 | 0.207(3) | 0.856(4) | 0.835(4) |
| T47 | 0.476(3) | 0.896(4) | 0.737(4) |
| T48 | 0.360(3) | 0.890(4) | 0.918(4) |
| T49 | 0.746(3) | 0.929(4) | 0.635(4) |
| T50 | 0.630(3) | 0.961(4) | 0.807(4) |
| T51 | 0.987(3) | 0.257(4) | 0.389(4) |
| T52 | 0.173(3) | 0.713(4) | 0.686(4) |

Table 4 shows the T-atom positions resulting from the Rietveld refinement of the x-ray data of the calcined form of UZM-55.

TABLE 4

Rietveld refinement results

| Site | X | Y | Z |
|---|---|---|---|
| T1 | 0.906(3) | 0.259(4) | 0.751(4) |
| T2 | 0.093(3) | 0.740(4) | 0.248(4) |
| T3 | 0.018(3) | 0.119(4) | 0.648(4) |
| T4 | 0.981(3) | 0.880(4) | 0.351(4) |
| T5 | 0.005(3) | 0.504(4) | 0.376(4) |
| T6 | 0.994(3) | 0.495(4) | 0.623(4) |
| T7 | 0.907(3) | 0.123(4) | 0.984(4) |
| T8 | 0.092(3) | 0.876(4) | 0.015(4) |
| T9 | 0.337(3) | 0.141(4) | 0.932(4) |
| T10 | 0.662(3) | 0.858(4) | 0.067(4) |
| T11 | 0.639(3) | 0.204(4) | 0.804(4) |
| T12 | 0.360(3) | 0.795(4) | 0.195(4) |
| T13 | 0.431(3) | 0.510(4) | 0.579(4) |
| T14 | 0.568(3) | 0.489(4) | 0.420(4) |
| T15 | 0.239(3) | 0.709(4) | 0.355(4) |
| T16 | 0.760(3) | 0.290(4) | 0.645(4) |
| T17 | 0.275(3) | 0.479(4) | 0.494(4) |
| T18 | 0.724(3) | 0.520(4) | 0.505(4) |
| T19 | 0.464(3) | 0.267(4) | 0.741(4) |
| T20 | 0.535(3) | 0.732(4) | 0.258(4) |
| T21 | 0.199(3) | 0.233(4) | 0.855(4) |
| T22 | 0.800(3) | 0.767(4) | 0.144(4) |
| T23 | 0.166(3) | 0.467(4) | 0.691(4) |
| T24 | 0.833(3) | 0.532(4) | 0.308(4) |
| T25 | 0.179(3) | 0.096(4) | 0.694(4) |
| T26 | 0.820(3) | 0.903(4) | 0.305(4) |
| T27 | 0.725(3) | 0.149(4) | 0.485(4) |
| T28 | 0.274(3) | 0.851(4) | 0.514(4) |
| T29 | 0.565(3) | 0.218(4) | 0.417(4) |
| T30 | 0.434(3) | 0.781(4) | 0.582(4) |
| T31 | 0.273(3) | 0.204(4) | 0.506(4) |
| T32 | 0.726(3) | 0.795(4) | 0.493(4) |
| T33 | 0.433(3) | 0.136(4) | 0.586(4) |
| T34 | 0.566(3) | 0.863(4) | 0.413(4) |
| T35 | 0.068(3) | 0.138(4) | 0.010(4) |
| T36 | 0.931(3) | 0.861(4) | 0.989(4) |
| T37 | 0.074(3) | 0.093(4) | 0.277(4) |
| T38 | 0.925(3) | 0.906(4) | 0.722(4) |
| T39 | 0.801(3) | 0.139(4) | 0.175(4) |
| T40 | 0.198(3) | 0.860(4) | 0.824(4) |
| T41 | 0.537(3) | 0.098(4) | 0.235(4) |
| T42 | 0.462(3) | 0.902(4) | 0.764(4) |
| T43 | 0.653(3) | 0.113(4) | 0.068(4) |
| T44 | 0.346(3) | 0.886(4) | 0.931(4) |
| T45 | 0.241(3) | 0.072(4) | 0.356(4) |
| T46 | 0.758(3) | 0.927(4) | 0.643(4) |
| T47 | 0.370(3) | 0.057(4) | 0.182(4) |
| T48 | 0.629(3) | 0.942(4) | 0.817(4) |
| T49 | 0.002(3) | 0.761(4) | 0.593(4) |
| T50 | 0.997(3) | 0.238(4) | 0.406(4) |
| T51 | 0.833(3) | 0.267(4) | 0.318(4) |
| T52 | 0.166(3) | 0.732(4) | 0.681(4) |

Tables 3 and 4 are shown with 52 T-sites. If the structure of UZM-55 is set in the space group P1 (#1), 52 independent T-sites are present. If the space group P-1 (#2) is instead utilized, an inversion center is present and only 26 independent T-sites are present although 52 T-sites still exist in a single unit cell. In an aspect, the structure of UZM-55 may be described in either the P1 or P-1 space group.

In an aspect, UZM-55 may comprise a faulted material. The UZM-55 of the current invention may possess planar faults consistent with streaking of reflections in electron diffraction images and asymmetric broadening of XRD patterns. The faulting may be visible in TEM images of UZM-55 when viewing down the 100 axis. The faulting may be consistent with an offset of approximately ⅓ of the b axis. In the MTW zeolite structure, a planar fault is known with a plane across the middle of the twelve-ring pore. For the case of the structure of UZM-55, a similar fault plane exists through the middle of the pore system (the a-b-plane), however, due to the low symmetry of UZM-55, the fault in UZM-55 is more likely a translation of the "butterfly unit" in the c-direction coupled with an inversion in the b-direction. These operations allow the $5^46$ "butterfly unit" to invert while the t-site connectivity is preserved. In crystallographic terms this faulting operation could be considered as a c-glide perpendicular to the b-axis which would generate a monoclinic unit cell if the fault were to occur 100% of the time. Butterfly units have a 6-ring which can be viewed as the body of a butterfly and four 5-rings which serve as the wings. Zeolite structures comprising butterfly units are discussed in Guo, et. al., Z. Kristallogr. 2015, 230, 301-9. Faulting in a zeolite structure may occur randomly or in a clustered fashion. In an aspect, the faulting in the UZM-55 structure may be random. In an aspect, faulting may occur about 20% of the time. Faulting may occur from 0% to about 100% of the time or may occur from 0% to about 50% of the time or may occur from 0% to about 30% of the time.

The crystalline UZM-55 zeolite of this invention may be used for separating mixtures of molecular species, removing contaminants through ion exchange and/or catalyzing various hydrocarbon conversion processes. Separation of molecular species can be based either on the molecular size (kinetic diameter) or on the degree of polarity of the molecular species. The separation process may comprise contacting at least two components with the UZM-55 zeolite material to generate at least one separated component.

In an aspect, a hydrocarbon stream may be contacted with a microporous crystalline zeolite having a channel system comprising 10-membered rings of tetrahedrally coordinated atoms and 12-membered rings of tetrahedrally coordinated atoms in a single channel wherein said contact is at conversion conditions to provide a converted hydrocarbon product comprising a hydrocarbon compound not present in the hydrocarbon stream. Hydrocarbon conversion processes include methanol to olefins, ethylene to propylene, oligomerization, isomerization of paraffins, paraffin cracking, conversion of an aromatic molecule to an aromatic molecule such as xylene isomerization, toluene disproportionation, ring opening and cracking to remove benzene co-boilers and alkylation of aromatics with paraffins In order to more fully illustrate the invention, the following examples are set forth. It is to be understood that the examples are only by way of illustration and are not intended as an undue limitation on the broad scope of the invention as set forth in the appended claims.

Example 1

419.33 grams of 1,6-dibromohexane and 330.56 grams of N-methylpiperidine were combined in a 2-L Teflon bottle along with 749.90 grams of DI $H_2O$. The mixture was stirred with a Heidolph mixer at 1600 RPM and transitioned from a two-layer solution to homogeneous white opaque mixture overnight. Heat was slowly added until a temperature of around 50-70° C. was obtained. Within 72 hours, the solution had become yellow and clear, which indicated the reaction had gone to completion. Partway through, the solution is yellow on top with unreacted clear material on the bottom. In this synthesis, 14.9 g of clear, unreacted material was separated using a separatory funnel. $^{13}$C-NMR analysis determined that a solution comprising 1,6-bis(N-methylpiperidinium) hexane dibromide had been synthesized.

Example 2

1000 g of solution from Example 1 was poured into a round-bottom flask along with excess silver (I) oxide and the solution was allowed to stir for 24 hours at room temperature. After the reaction was complete (24-48 hours), the resulting material was filtered to remove the solid silver bromide and was allowed to sit in direct sunlight so that any remaining silver bromide would precipitate and fall out of solution. The filter/sun cycle was repeated four times before the solution remained clear and was deemed to be usable. It was then sent for water analysis and shown to comprise 67.4% water.

Example 3

Figure 4:
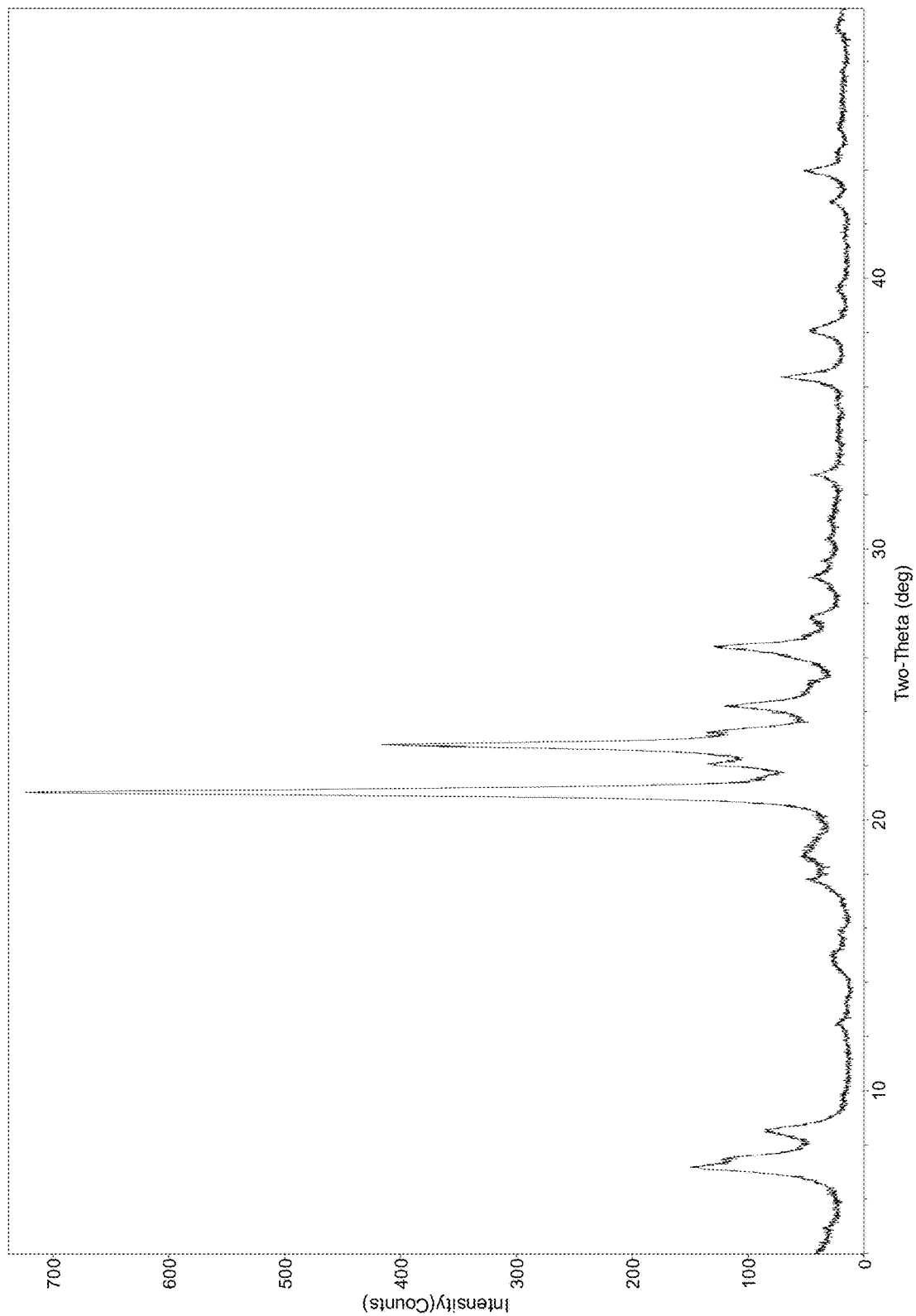
FIG. 4 is an XRD pattern of the UZM-55 zeolite formed in Example 3. This pattern shows the UZM-55 zeolite in the as-synthesized form.
Figure 5:
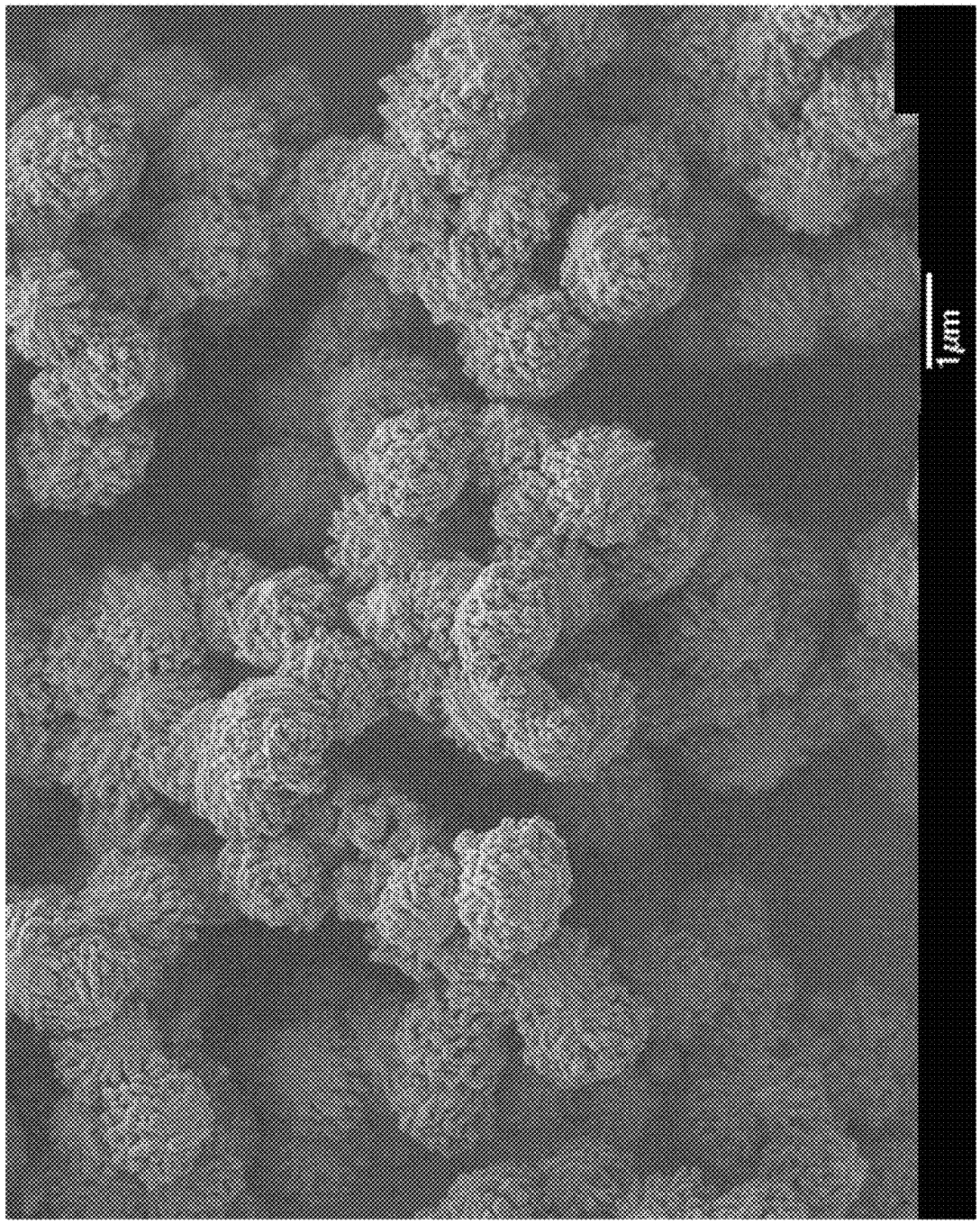
FIG. 5 is a high resolution SEM image of the UZM-55 zeolite formed in Example 3 at 1 μm resolution.
Figure 6:
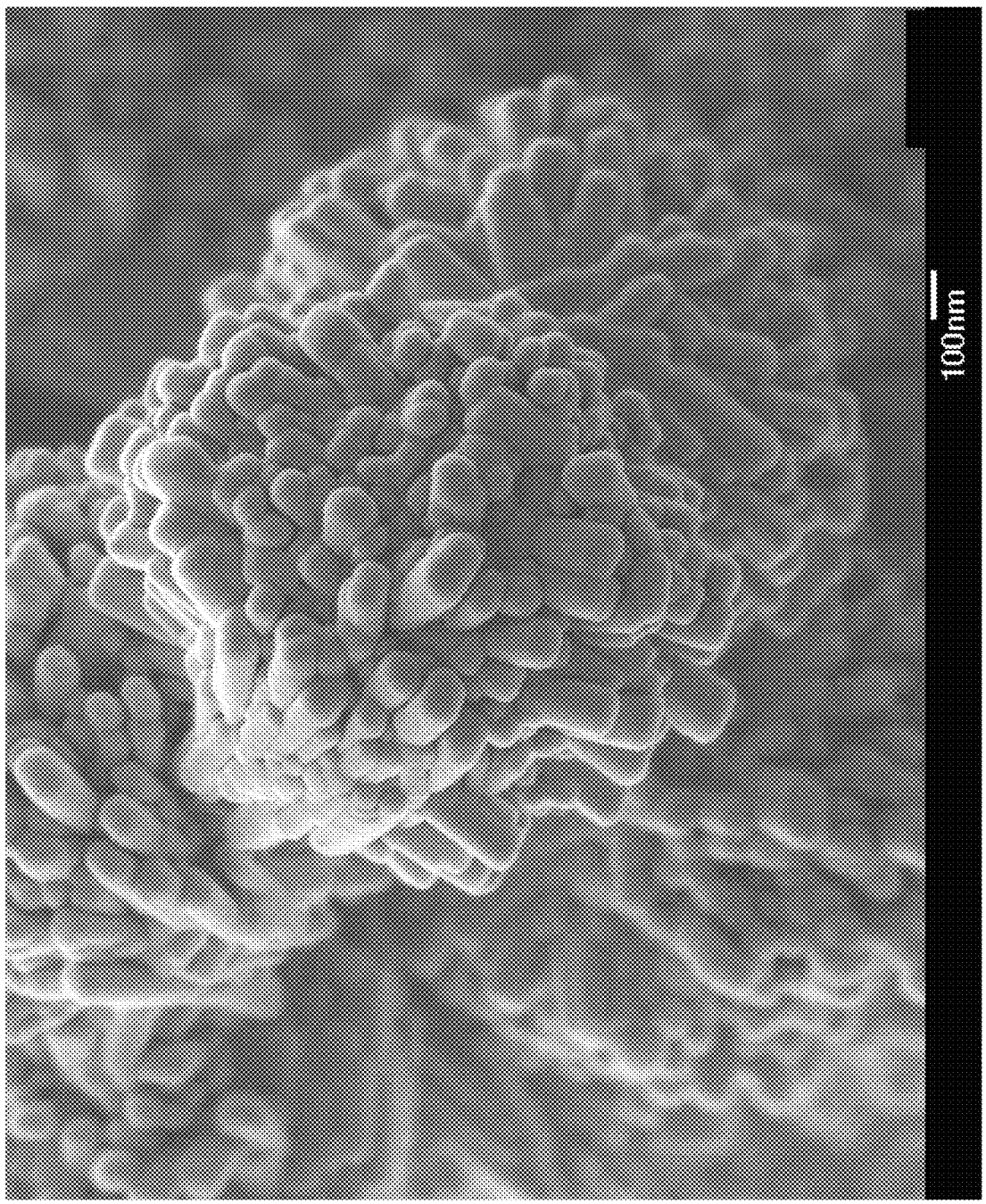
FIG. 6 is a high resolution SEM image of the UZM-55 zeolite formed in Example 3 at 100 nm resolution.
Figure 7:
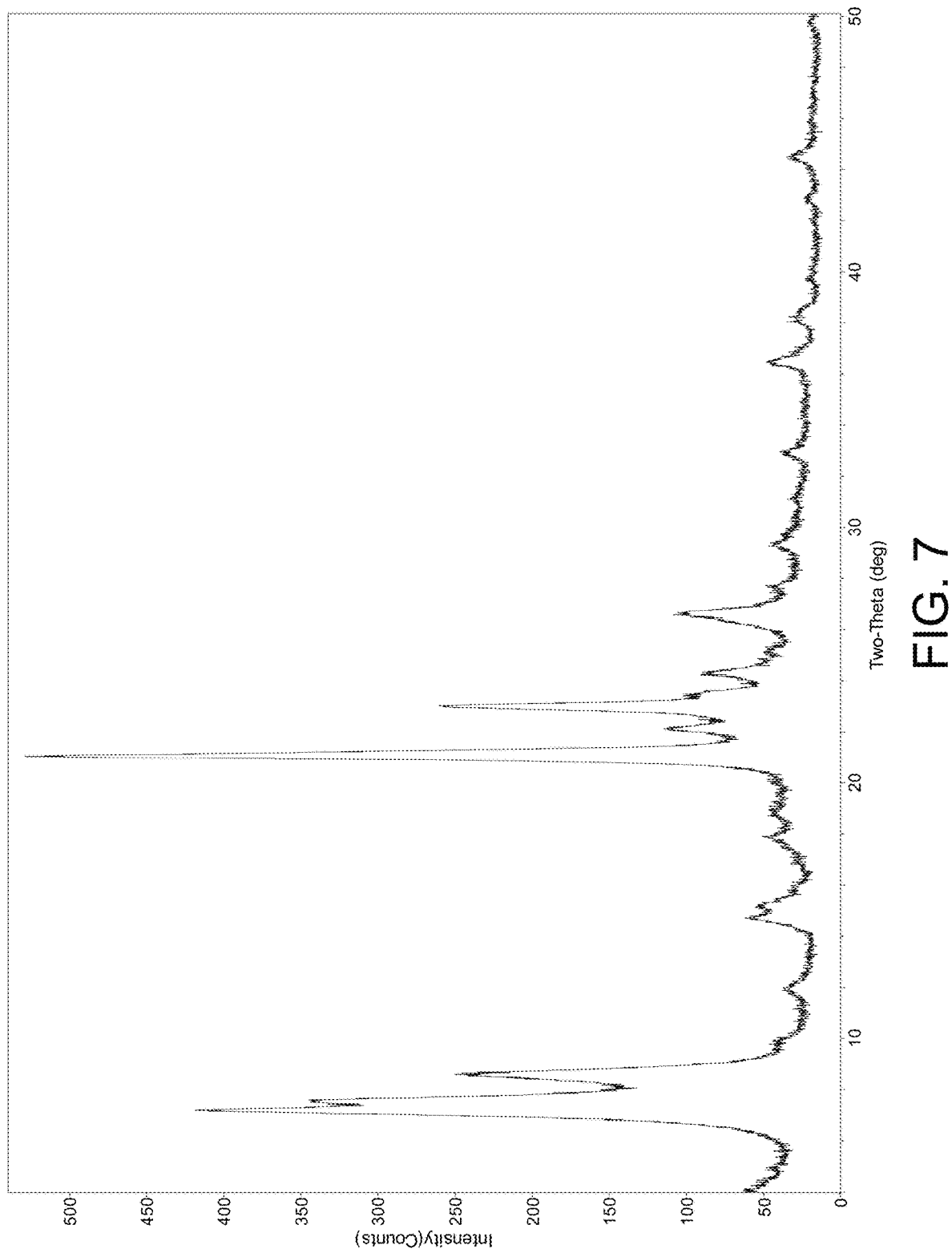
FIG. 7 is also an XRD pattern of the UZM-55 zeolite formed in Example 3. This pattern shows the UZM-55 zeolite after calcination.

50 g LudoxAS-40 was stirred into 48.74 g of the Example 2 solution, followed by the addition of 106.85 g water. After mixing thoroughly, this synthesis solution was transferred to a 300 cc stirred autoclave and digested for 6 days at 160° while stirring at 250 rpm. The product was dried. Analysis shows a LOI of 12.8 wt %, Si=47.2 wt %, Al=0.045 wt %, Na=0.04 wt % 7.47 wt % C, 0.976 wt % N for a carbon to nitrogen ratio of 9. The XRD pattern is shown in FIG. 4. High resolution SEM images are shown at two different length scales in FIGS. 5 and 6 respectively. The sample was then calcined under air for 4 hours at 600° C. Analysis shows a BET SA of 273 $m^2/g$, Langmuir SA of 400 $m^2/g$, total pore volume of 0.225 cc/g, and a micropore volume of 0.107 cc/g. The XRD pattern is shown in FIG. 7.

Example 4

43.33 grams LudoxAS-40 was stirred into a mixture of 1.63 grams of a 10 wt % KOH solution in water and 40.71 grams Example 2 product. 100.71 grams DI $H_2O$ was then stirred in. After mixing thoroughly 0.18 g. $H_3BO_3$ was added. The resulting synthesis mixture was loaded into a 300 cc stirred autoclave and digested for 6 days at 160° C. stirring at 250 rpm. The product was dried. Elemental analysis showed 47.1% Si (V.F.), 0.14% B with an LOI of 13.4%, C/N=9.53. XRD analysis identified the product as UZM-55.

Example 5

0.11 grams aluminum hydroxide (Pfaltz & Bauer) was combined with 41.12 grams of the Example 2 solution and stirred until all of the alumina had dissolved. 43.48 grams of Ludox AS-40 was then added along with 94.14 grams of DI $H_2O$. The resulting synthesis mixture was loaded into a 300 cc stirred autoclave and digested for 6 days at 160° C. stirring at 250 rpm. The product was dried. Elemental analysis shows 46.5% Si (V.F.), 0.31% Al with an LOI of 14.3%, C/N=9.55. XRD analysis identified the product as UZM-55. A portion of this product was calcined at 600° C. for 4 hours. Analysis shows a BET SA of 301 $m^2/g$, total pore volume of 0.235 cc/g, and a micropore volume of 0.120 cc/g.

Example 6

Figure 8:
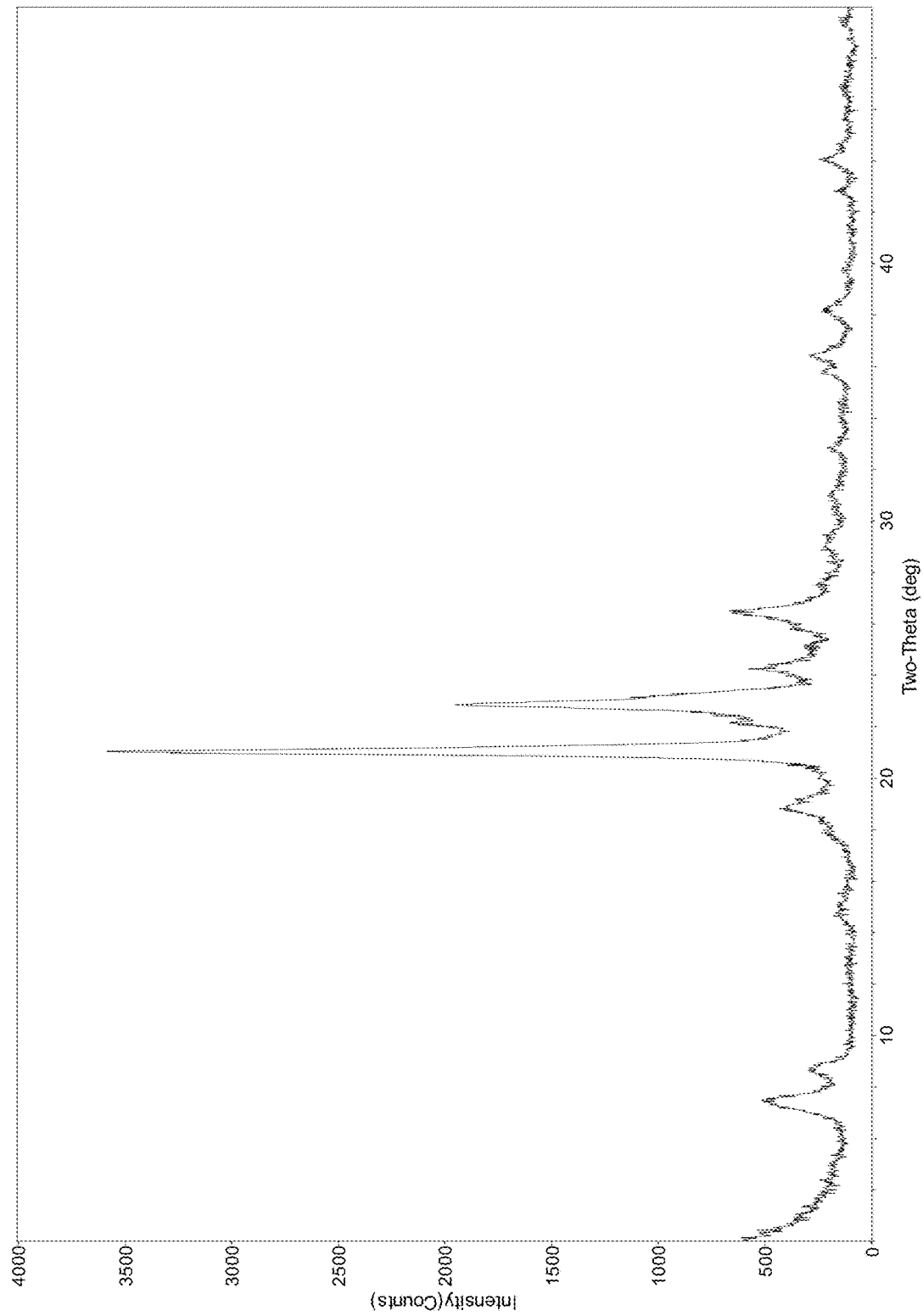
FIG. 8 is an XRD pattern of the UZM-55 zeolite formed in Example 6. This pattern shows the UZM-55 zeolite in the as-synthesized form

1.25 grams of aluminum hydroxide (Pfaltz & Bauer) was combined with 274.29 grams of the Example 2 solution and stirred until all of the alumina had dissolved. 290.00 grams of Ludox AS-40 was then added along with 627.92 grams of DI $H_2O$. 0.79 g of the as-synthesized Example 3 product and 0.36 g of the calcined Example 3 product were then stirred in. The resulting synthesis mixture was loaded into a 2-L stirred autoclave and digested at 160° C. at 250 RPM for 210 hours. The resulting product was isolated via centrifugation and dried at 100° C. to remove any residual water. Analysis showed $SiO_2/Al_2O_3$=189, 40 ppm Na and LOI=13.0 wt %. The x-ray diffraction pattern is shown in FIG. 8. A portion of this product was calcined at 600° C. for 4 hours. Analysis shows a BET SA of 342 $m^2/g$, total pore volume of 0.339 cc/g, and a micropore volume of 0.112 cc/g.

Example 7

12.71 grams of 1,6-dibromohexane and 10.02 grams of N-Methylpiperidine were combined in a 125 cc Teflon bottle along with 22.72 grams of DI $H_2O$. The mixture was stirred with a Heidolph mixer at 1600 RPM over the weekend and transitioned from a two-layer solution to homogeneous white opaque mixture overnight to a clear yellow solution. This yellow solution was combined with 419.33 grams of 1,6-dibromohexane, 330.56 grams of N-Methylpiperidine and 749.90 grams of DI $H_2O$ in a 2 L Teflon bottle and stirred with the Heidolph stirrer. After 2 days, clear liquid still existed on the bottom, so small quantities of N-methylpiperidine were added over the next two days while stirring. After the weekend, the solution was completely yellow colored. $^{13}$C-NMR analysis determined that a solution comprising 1,6-bis(N-Methylpiperidinium)hexane dibromide had been synthesized.

Example 8

1000 grams of solution from Example 7 was poured into a round-bottom flask along with excess silver(I) oxide and the solution was allowed to stir for 24 hours at room temperature. After the reaction was complete (24-48 hours), the resulting material was filtered to remove the solid silver bromide and was allowed to sit in direct sunlight so that any remaining silver bromide would precipitate and fall out of solution. The filter/sun cycle was repeated four times before the solution remained clear and was deemed to be usable. It was then sent for water analysis and shown to comprise 67.4% water.

Example 9

16.66 grams of Ludox AS-40 was stirred into 16.25 g of the Example 8 solution, followed by the addition of 35.61 g water. After mixing thoroughly, this synthesis solution was transferred into 45 cc static autoclave and digested for 3 days at 175° C. The product was dried. XRD analysis identified the product as UZM-55.

Example 10

2 moles (508.29 grams) of 1,6-dibromohexane and 4 moles (400.69 grams) of N-methylpiperdine were combined in a 2-L Teflon bottle along with 908.98 grams of DI $H_2O$. The mixture was stirred with a Heidolph mixer at 1600 RPM and transitioned from a two-layer solution to a homogenous white opaque solution overnight. Heat was slowly added until a temperature of around 50-70° C. was obtained. Within 48 hours, the solution had become yellow and clear, which indicated the reaction had gone to completion.

Example 11

1221.4 grams of solution from Example 10 was poured into a round-bottom flask along with excess silver(I) oxide and the solution was allowed to stir for 24 hours at room temperature. After the reaction was complete (24-48 hours), the resulting material was filtered to remove the solid silver precipitate and was allowed to sit in direct sunlight so that any remaining silver bromide would fall out of solution. The filter/sun cycle was repeated four times before the solution remained clear and was deemed to be usable. It was then sent for water analysis and shown to comprise 67.6% water.

Example 12

0.63 grams aluminum isopropoxide (98%, Sigma Aldrich) was combined with 42.65 grams of the Example 11 solution and stirred until all of the alumina was dissolved. 43.48 grams of Ludox AS-40 was then added along with 92.62 grams of DI $H_2O$. 0.41 grams of pure $SiO_2$ UZM-55 was then stirred in. The resulting synthesis mixture was loaded into a 300 cc stirred autoclave and digested for 8 days at 160° C. stirring at 250 RPM. XRD analysis identified the product as UZM-55 with a MTW impurity.

Example 13

Figure 9:
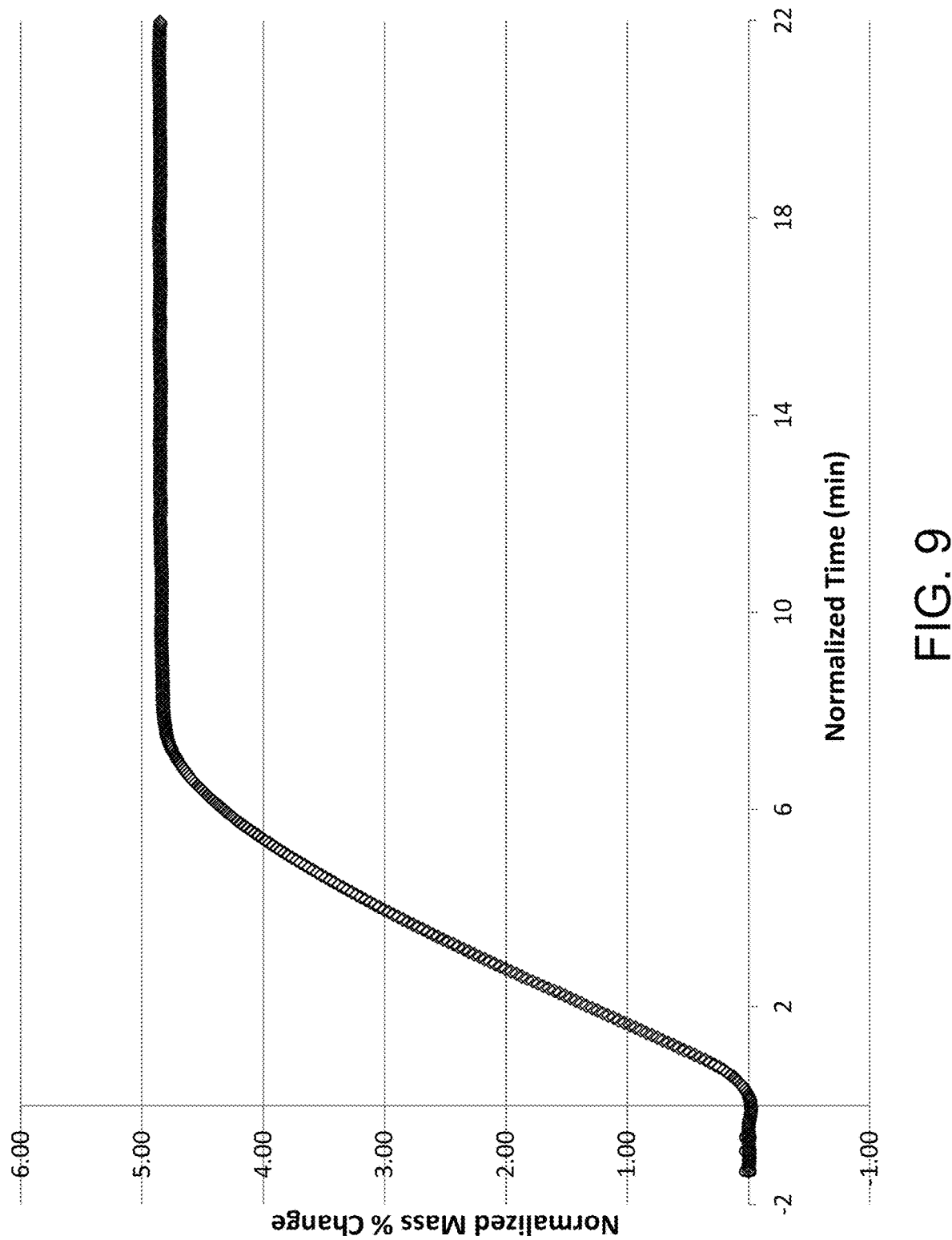
FIG. 9 is a graph of the mass fraction of n-nonane adsorbed by UZM-55 as a function of time of exposure as described in Example 13.

In addition to catalyst applications, UZM-55 may be utilized for adsorption. To adsorb n-nonane, approximately 10 mg of UZM-55 was loaded into a pan and loaded into the TGA instrument. The sample was ramped 20° C./min to 350° C., held for 10 minutes, cooled to 120° C., and waited for the sample weight to stabilize before a flow of $N_2$ containing n-nonane at 1 atm was introduced until the weight stabilized. To achieve the proper partial pressure, a gas split of 127 mL/min $N_2$, to 72 mL/min of n-nonane saturated $N_2$ having passed through a saturator containing n-nonane maintained at 25° C. was used. The weight percent n-nonane adsorbed per weight UZM-55 is shown in FIG. 9. UZM-55 may adsorb greater than 4.5 wt % n-nonane or greater than 4.75 wt % n-nonane. In this experiment, UZM-55 adsorbed 4.88 wt % n-nonane. The uptake rate of n-nonane by UZM-55 in this experiment was 0.86 mg n-nonane per minute. The uptake rate may be greater than 0.7 mg/min or greater than 0.75 mg/min or greater than 0.80 mg/min.

Example 14

MTO Data

Figure 10:
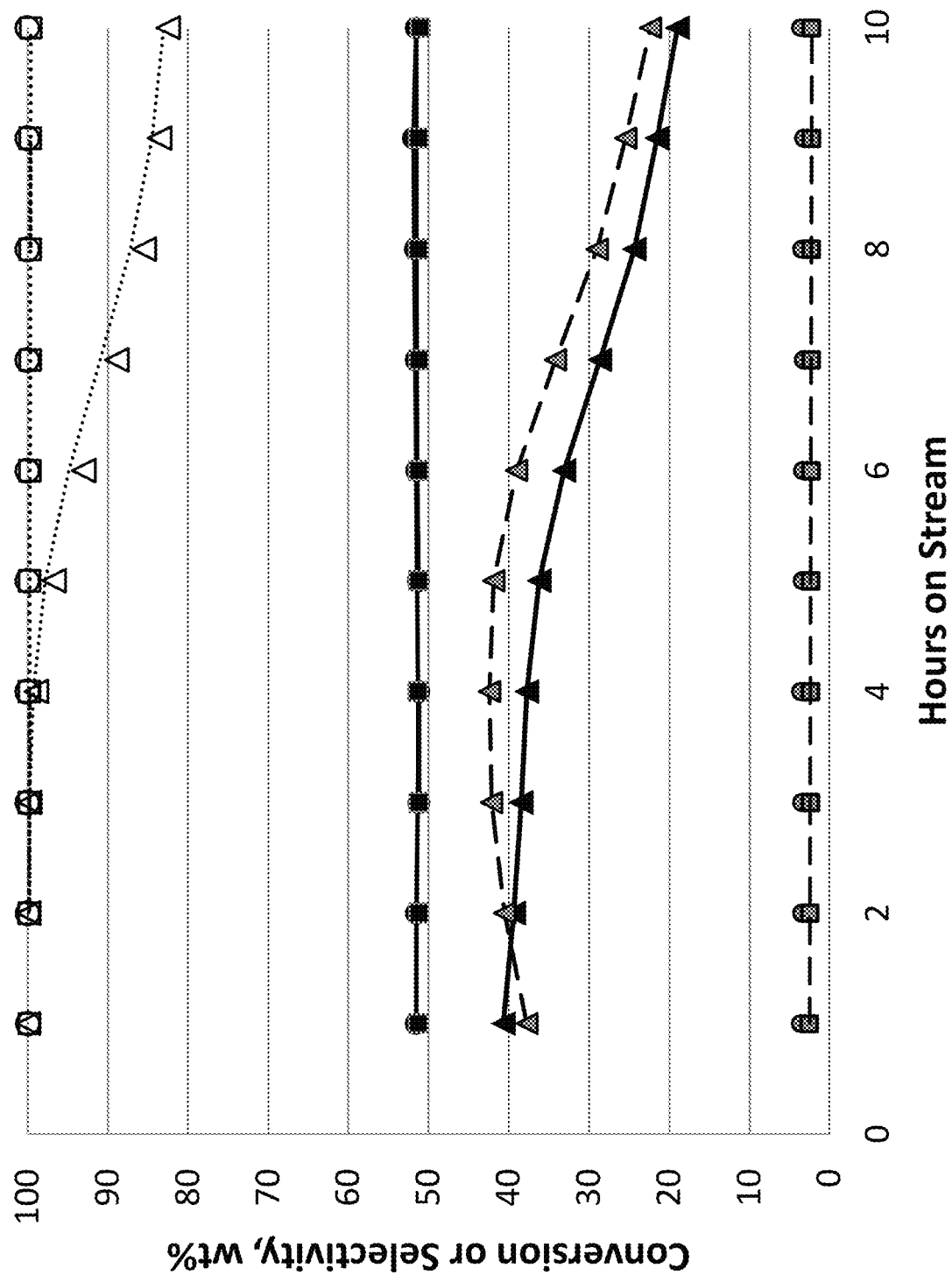
FIG. 10 is a graph of the conversion of methanol to hydrocarbons and selectivity to those hydrocarbons as a function of time on stream for both UZM-55 and a SAPO-34 reference as described in Example 14.

The methanol to olefin (MTO) breakthrough test was run at constant temperature, 450° C., and constant flow rate, 135 cc/min. Prior to the run, a pretreatment in $N_2$ for 30 minutes at 500° C. was carried out. Three catalysts were evaluated, the UZM-55 of Example 5, the UZM-55 of Example 6 and a reference SAPO-34 molecular sieve and the results shown in the table below as a function of the time on stream. UZM-55 displays an essentially constant conversion of nearly 100% throughout the test, with a nearly constant selectivity to propylene of between 50 and 55 wt %. Additionally, the selectivity to ethylene is very low over UZM-55 at less than 5 wt % or less than 4 wt % or less than 3 wt %. FIG. 10 shows the results of the run graphically, with open markers with dotted lines indicating conversion, gray markers with black outline and dashed lines indicating ethylene selectivity, and black markers with solid black lines indicating propylene selectivity. Triangles indicate the SAPO-34 reference, circles the catalyst of Example 6, and squares the catalyst of Example 5.

TABLE 5

| Hrs on Stream | SAPO-34 | Example 5 | Example 6 | SAPO-34 | Example 5 | Example 6 | SAPO-34 | Example 5 | Example 6 |
|---|---|---|---|---|---|---|---|---|---|
| | | Conversion | | | C3 = Selectivity | | | C2 = Selectivity | |
| 1 | 100.0 | 99.8 | 99.9 | 40.7 | 51.3 | 51.5 | 37.8 | 2.5 | 3.6 |
| 2 | 99.9 | 99.8 | 100.0 | 39.4 | 51.2 | 51.5 | 40.5 | 2.4 | 3.5 |
| 3 | 99.7 | 99.8 | 100.0 | 38.5 | 51.2 | 51.2 | 42.1 | 2.4 | 3.6 |
| 4 | 98.9 | 99.8 | 100.0 | 37.7 | 51.3 | 51.2 | 42.4 | 2.4 | 3.5 |
| 5 | 96.7 | 99.7 | 100.0 | 36.2 | 51.3 | 51.2 | 41.9 | 2.3 | 3.4 |
| 6 | 93.0 | 99.7 | 100.0 | 33.1 | 51.3 | 51.4 | 39.0 | 2.3 | 3.4 |
| 7 | 88.9 | 99.7 | 100.0 | 28.7 | 51.2 | 51.5 | 34.2 | 2.3 | 3.3 |
| 8 | 85.5 | 99.6 | 100.0 | 24.4 | 51.3 | 51.6 | 29.0 | 2.3 | 3.5 |
| 9 | 83.6 | 99.6 | 100.0 | 21.5 | 51.2 | 51.9 | 25.4 | 2.2 | 3.2 |
| 10 | 82.5 | 99.6 | 100.0 | 19.0 | 51.1 | 51.5 | 22.3 | 2.2 | 3.6 |

Specific Embodiments

While the following is described in conjunction with specific embodiments, it will be understood that this description is intended to illustrate and not limit the scope of the preceding description and the appended claims.

A first embodiment of the invention is a microporous crystalline zeolite having a channel system comprising 10-membered rings of tetrahedrally coordinated atoms and 12-membered rings of tetrahedrally coordinated atoms in a single channel. An embodiment of the invention is one, any or all of prior embodiments in this paragraph up through the first embodiment wherein the channel system is one-dimensional. An embodiment of the invention is one, any or all of prior embodiments in this paragraph up through the first embodiment wherein the tetrahedrally coordinated atoms are Si, Al or E atoms and further comprise a framework of tetrahedral atoms bridged by oxygen atoms, the tetrahedral atom framework being defined by a unit cell of a=17.80 Å, b=12.23 Å, c=12.93 Å, alpha=71.79°, beta=88.16°, gamma=90.25° with fractional atomic coordinates of the tetrahedral atoms shown in Table 3 wherein each cell axis length may vary within +/−0.75 Å, each cell angle may vary within about +/−1.0° and each t-site position may vary within about +/−0.75 Å as shown in Table 3 below:

TABLE 3

| Calcined, optimized | | | |
|---|---|---|---|
| Site | X | Y | Z |
| T1 | 0.913(3) | 0.270(4) | 0.745(4) |
| T2 | 0.001(3) | 0.121(4) | 0.633(4) |
| T3 | 0.995(3) | 0.512(4) | 0.373(4) |
| T4 | 0.911(3) | 0.129(4) | 0.983(4) |
| T5 | 0.347(3) | 0.135(4) | 0.940(4) |
| T6 | 0.623(3) | 0.208(4) | 0.828(4) |
| T7 | 0.432(3) | 0.507(4) | 0.581(4) |
| T8 | 0.247(3) | 0.697(4) | 0.335(4) |
| T9 | 0.275(3) | 0.466(4) | 0.500(4) |
| T10 | 0.462(3) | 0.278(4) | 0.765(4) |
| T11 | 0.185(3) | 0.223(4) | 0.870(4) |
| T12 | 0.167(3) | 0.456(4) | 0.701(4) |
| T13 | 0.164(3) | 0.094(4) | 0.694(4) |
| T14 | 0.709(3) | 0.175(4) | 0.498(4) |
| T15 | 0.550(3) | 0.239(4) | 0.417(4) |
| T16 | 0.280(3) | 0.212(4) | 0.514(4) |
| T17 | 0.434(3) | 0.141(4) | 0.606(4) |
| T18 | 0.075(3) | 0.106(4) | 0.057(4) |
| T19 | 0.089(3) | 0.103(4) | 0.296(4) |
| T20 | 0.792(3) | 0.143(4) | 0.164(4) |
| T21 | 0.523(3) | 0.103(4) | 0.262(4) |
| T22 | 0.639(3) | 0.109(4) | 0.081(4) |
| T23 | 0.253(3) | 0.070(4) | 0.364(4) |
| T24 | 0.369(3) | 0.038(4) | 0.192(4) |
| T25 | 0.012(3) | 0.742(4) | 0.610(4) |
| T26 | 0.826(3) | 0.286(4) | 0.313(4) |
| T27 | 0.086(3) | 0.729(4) | 0.254(4) |
| T28 | 0.998(3) | 0.879(4) | 0.367(4) |
| T29 | 0.004(3) | 0.487(4) | 0.626(4) |
| T30 | 0.088(3) | 0.870(4) | 0.016(4) |
| T31 | 0.653(3) | 0.864(4) | 0.059(4) |
| T32 | 0.376(3) | 0.791(4) | 0.171(4) |
| T33 | 0.567(3) | 0.492(4) | 0.418(4) |
| T34 | 0.752(3) | 0.302(4) | 0.664(4) |
| T35 | 0.724(3) | 0.534(4) | 0.499(4) |
| T36 | 0.537(3) | 0.721(4) | 0.234(4) |
| T37 | 0.814(3) | 0.776(4) | 0.129(4) |
| T38 | 0.832(3) | 0.543(4) | 0.299(4) |
| T39 | 0.835(3) | 0.905(4) | 0.305(4) |
| T40 | 0.290(3) | 0.824(4) | 0.501(4) |
| T41 | 0.449(3) | 0.760(4) | 0.582(4) |
| T42 | 0.719(3) | 0.787(4) | 0.485(4) |
| T43 | 0.565(3) | 0.858(4) | 0.393(4) |

TABLE 3-continued

| Calcined, optimized | | | |
|---|---|---|---|
| Site | X | Y | Z |
| T44 | 0.924(3) | 0.893(4) | 0.942(4) |
| T45 | 0.910(3) | 0.896(4) | 0.704(4) |
| T46 | 0.207(3) | 0.856(4) | 0.835(4) |
| T47 | 0.476(3) | 0.896(4) | 0.737(4) |
| T48 | 0.360(3) | 0.890(4) | 0.918(4) |
| T49 | 0.746(3) | 0.929(4) | 0.635(4) |
| T50 | 0.630(3) | 0.961(4) | 0.807(4) |
| T51 | 0.987(3) | 0.257(4) | 0.389(4) |
| T52 | 0.173(3) | 0.713(4) | 0.686(4) |

An embodiment of the invention is one, any or all of prior embodiments in this paragraph up through the first embodiment wherein the tetrahedrally coordinated atoms are Si, Al or E atoms and further comprise a framework of tetrahedral atoms bridged by oxygen atoms, the tetrahedral atom framework being defined by a unit cell of a=17.80 Å, b=12.23 Å, c=12.93 Å, alpha=71.79°, beta=88.16°, gamma=90.25° with fractional atomic coordinates of the tetrahedral atoms shown in Table 4 wherein each cell axis length may vary within +/−0.75 Å, each cell angle may vary within about +/−1.0° and each t-site position may vary within about +/−0.75 Å as shown in Table 4.

TABLE 4

| Rietveld refinement results | | | |
|---|---|---|---|
| Site | X | Y | Z |
| T1 | 0.906(3) | 0.259(4) | 0.751(4) |
| T2 | 0.093(3) | 0.740(4) | 0.248(4) |
| T3 | 0.018(3) | 0.119(4) | 0.648(4) |
| T4 | 0.981(3) | 0.880(4) | 0.351(4) |
| T5 | 0.005(3) | 0.504(4) | 0.376(4) |
| T6 | 0.994(3) | 0.495(4) | 0.623(4) |
| T7 | 0.907(3) | 0.123(4) | 0.984(4) |
| T8 | 0.092(3) | 0.876(4) | 0.015(4) |
| T9 | 0.337(3) | 0.141(4) | 0.932(4) |
| T10 | 0.662(3) | 0.858(4) | 0.067(4) |
| T11 | 0.639(3) | 0.204(4) | 0.804(4) |
| T12 | 0.360(3) | 0.795(4) | 0.195(4) |
| T13 | 0.431(3) | 0.510(4) | 0.579(4) |
| T14 | 0.568(3) | 0.489(4) | 0.420(4) |
| T15 | 0.239(3) | 0.709(4) | 0.355(4) |
| T16 | 0.760(3) | 0.290(4) | 0.645(4) |
| T17 | 0.275(3) | 0.479(4) | 0.494(4) |
| T18 | 0.724(3) | 0.520(4) | 0.505(4) |
| T19 | 0.464(3) | 0.267(4) | 0.741(4) |
| T20 | 0.535(3) | 0.732(4) | 0.258(4) |
| T21 | 0.199(3) | 0.233(4) | 0.855(4) |
| T22 | 0.800(3) | 0.767(4) | 0.144(4) |
| T23 | 0.166(3) | 0.467(4) | 0.691(4) |
| T24 | 0.833(3) | 0.532(4) | 0.308(4) |
| T25 | 0.179(3) | 0.096(4) | 0.694(4) |
| T26 | 0.820(3) | 0.903(4) | 0.305(4) |
| T27 | 0.725(3) | 0.149(4) | 0.485(4) |
| T28 | 0.274(3) | 0.851(4) | 0.514(4) |
| T29 | 0.565(3) | 0.218(4) | 0.417(4) |
| T30 | 0.434(3) | 0.781(4) | 0.582(4) |
| T31 | 0.273(3) | 0.204(4) | 0.506(4) |
| T32 | 0.726(3) | 0.795(4) | 0.493(4) |
| T33 | 0.433(3) | 0.136(4) | 0.586(4) |
| T34 | 0.566(3) | 0.863(4) | 0.413(4) |
| T35 | 0.068(3) | 0.138(4) | 0.010(4) |
| T36 | 0.931(3) | 0.861(4) | 0.989(4) |
| T37 | 0.074(3) | 0.093(4) | 0.277(4) |
| T38 | 0.925(3) | 0.906(4) | 0.722(4) |
| T39 | 0.801(3) | 0.139(4) | 0.175(4) |
| T40 | 0.198(3) | 0.860(4) | 0.824(4) |
| T41 | 0.537(3) | 0.098(4) | 0.235(4) |
| T42 | 0.462(3) | 0.902(4) | 0.764(4) |
| T43 | 0.653(3) | 0.113(4) | 0.068(4) |

An embodiment of the invention is one, any or all of the prior embodiments in this paragraph up through the first embodiment wherein the microporous crystalline zeolite comprising a framework of tetrahedral atoms bridged by oxygen atoms, the tetrahedral atom framework being defined by a unit cell of a=17.80 Å, b=12.23 Å, c=12.93 Å, alpha=71.79°, beta=88.16°, gamma=90.25° with fractional atomic coordinates of the tetrahedral atoms shown in Table 3 or Table 4 wherein each cell axis length may vary within +/−0.75 Å, each cell angle may vary within about +/−1.0° and each t-site position may vary within about +/−0.75 Å wherein Tables 3 and 4 is as follows:

TABLE 3

| | Calcined, optimized | | |
|---|---|---|---|
| Site | X | Y | Z |
| T1 | 0.913(3) | 0.270(4) | 0.745(4) |
| T2 | 0.001(3) | 0.121(4) | 0.633(4) |
| T3 | 0.995(3) | 0.512(4) | 0.373(4) |
| T4 | 0.911(3) | 0.129(4) | 0.983(4) |
| T5 | 0.347(3) | 0.135(4) | 0.940(4) |
| T6 | 0.623(3) | 0.208(4) | 0.828(4) |
| T7 | 0.432(3) | 0.507(4) | 0.581(4) |
| T8 | 0.247(3) | 0.697(4) | 0.335(4) |
| T9 | 0.275(3) | 0.466(4) | 0.500(4) |
| T10 | 0.462(3) | 0.278(4) | 0.765(4) |
| T11 | 0.185(3) | 0.223(4) | 0.870(4) |
| T12 | 0.167(3) | 0.456(4) | 0.701(4) |
| T13 | 0.164(3) | 0.094(4) | 0.694(4) |
| T14 | 0.709(3) | 0.175(4) | 0.498(4) |
| T15 | 0.550(3) | 0.239(4) | 0.417(4) |
| T16 | 0.280(3) | 0.212(4) | 0.514(4) |
| T17 | 0.434(3) | 0.141(4) | 0.606(4) |
| T18 | 0.075(3) | 0.106(4) | 0.057(4) |
| T19 | 0.089(3) | 0.103(4) | 0.296(4) |
| T20 | 0.792(3) | 0.143(4) | 0.164(4) |
| T21 | 0.523(3) | 0.103(4) | 0.262(4) |
| T22 | 0.639(3) | 0.109(4) | 0.081(4) |
| T23 | 0.253(3) | 0.070(4) | 0.364(4) |
| T24 | 0.369(3) | 0.038(4) | 0.192(4) |
| T25 | 0.012(3) | 0.742(4) | 0.610(4) |
| T26 | 0.826(3) | 0.286(4) | 0.313(4) |
| T27 | 0.086(3) | 0.729(4) | 0.254(4) |
| T28 | 0.998(3) | 0.879(4) | 0.367(4) |
| T29 | 0.004(3) | 0.487(4) | 0.626(4) |
| T30 | 0.088(3) | 0.870(4) | 0.016(4) |
| T31 | 0.653(3) | 0.864(4) | 0.059(4) |
| T32 | 0.376(3) | 0.791(4) | 0.171(4) |
| T33 | 0.567(3) | 0.492(4) | 0.418(4) |
| T34 | 0.752(3) | 0.302(4) | 0.664(4) |
| T35 | 0.724(3) | 0.534(4) | 0.499(4) |
| T36 | 0.537(3) | 0.721(4) | 0.234(4) |
| T37 | 0.814(3) | 0.776(4) | 0.129(4) |
| T38 | 0.832(3) | 0.543(4) | 0.299(4) |
| T39 | 0.835(3) | 0.905(4) | 0.305(4) |
| T40 | 0.290(3) | 0.824(4) | 0.501(4) |
| T41 | 0.449(3) | 0.760(4) | 0.582(4) |
| T42 | 0.719(3) | 0.787(4) | 0.485(4) |
| T43 | 0.565(3) | 0.858(4) | 0.393(4) |
| T44 | 0.924(3) | 0.893(4) | 0.942(4) |
| T45 | 0.910(3) | 0.896(4) | 0.704(4) |
| T46 | 0.207(3) | 0.856(4) | 0.835(4) |
| T47 | 0.476(3) | 0.896(4) | 0.737(4) |
| T48 | 0.360(3) | 0.890(4) | 0.918(4) |
| T49 | 0.746(3) | 0.929(4) | 0.635(4) |
| T50 | 0.630(3) | 0.961(4) | 0.807(4) |
| T51 | 0.987(3) | 0.257(4) | 0.389(4) |
| T52 | 0.173(3) | 0.713(4) | 0.686(4) |

TABLE 4

| | Rietveld refinement results | | |
|---|---|---|---|
| Site | X | Y | Z |
| T1 | 0.906(3) | 0.259(4) | 0.751(4) |
| T2 | 0.093(3) | 0.740(4) | 0.248(4) |
| T3 | 0.018(3) | 0.119(4) | 0.648(4) |
| T4 | 0.981(3) | 0.880(4) | 0.351(4) |
| T5 | 0.005(3) | 0.504(4) | 0.376(4) |
| T6 | 0.994(3) | 0.495(4) | 0.623(4) |
| T7 | 0.907(3) | 0.123(4) | 0.984(4) |
| T8 | 0.092(3) | 0.876(4) | 0.015(4) |
| T9 | 0.337(3) | 0.141(4) | 0.932(4) |
| T10 | 0.662(3) | 0.858(4) | 0.067(4) |
| T11 | 0.639(3) | 0.204(4) | 0.804(4) |
| T12 | 0.360(3) | 0.795(4) | 0.195(4) |
| T13 | 0.431(3) | 0.510(4) | 0.579(4) |
| T14 | 0.568(3) | 0.489(4) | 0.420(4) |
| T15 | 0.239(3) | 0.709(4) | 0.355(4) |
| T16 | 0.760(3) | 0.290(4) | 0.645(4) |
| T17 | 0.275(3) | 0.479(4) | 0.494(4) |
| T18 | 0.724(3) | 0.520(4) | 0.505(4) |
| T19 | 0.464(3) | 0.267(4) | 0.741(4) |
| T20 | 0.535(3) | 0.732(4) | 0.258(4) |
| T21 | 0.199(3) | 0.233(4) | 0.855(4) |
| T22 | 0.800(3) | 0.767(4) | 0.144(4) |
| T23 | 0.166(3) | 0.467(4) | 0.691(4) |
| T24 | 0.833(3) | 0.532(4) | 0.308(4) |
| T25 | 0.179(3) | 0.096(4) | 0.694(4) |
| T26 | 0.820(3) | 0.903(4) | 0.305(4) |
| T27 | 0.725(3) | 0.149(4) | 0.485(4) |
| T28 | 0.274(3) | 0.851(4) | 0.514(4) |
| T29 | 0.565(3) | 0.218(4) | 0.417(4) |
| T30 | 0.434(3) | 0.781(4) | 0.582(4) |
| T31 | 0.273(3) | 0.204(4) | 0.506(4) |
| T32 | 0.726(3) | 0.795(4) | 0.493(4) |
| T33 | 0.433(3) | 0.136(4) | 0.586(4) |
| T34 | 0.566(3) | 0.863(4) | 0.413(4) |
| T35 | 0.068(3) | 0.138(4) | 0.010(4) |
| T36 | 0.931(3) | 0.861(4) | 0.989(4) |
| T37 | 0.074(3) | 0.093(4) | 0.277(4) |
| T38 | 0.925(3) | 0.906(4) | 0.722(4) |
| T39 | 0.801(3) | 0.139(4) | 0.175(4) |
| T40 | 0.198(3) | 0.860(4) | 0.824(4) |
| T41 | 0.537(3) | 0.098(4) | 0.235(4) |
| T42 | 0.462(3) | 0.902(4) | 0.764(4) |
| T43 | 0.653(3) | 0.113(4) | 0.068(4) |
| T44 | 0.346(3) | 0.886(4) | 0.931(4) |
| T45 | 0.241(3) | 0.072(4) | 0.356(4) |
| T46 | 0.758(3) | 0.927(4) | 0.643(4) |
| T47 | 0.370(3) | 0.057(4) | 0.182(4) |
| T48 | 0.629(3) | 0.942(4) | 0.817(4) |
| T49 | 0.002(3) | 0.761(4) | 0.593(4) |
| T50 | 0.997(3) | 0.238(4) | 0.406(4) |
| T51 | 0.833(3) | 0.267(4) | 0.318(4) |
| T52 | 0.166(3) | 0.732(4) | 0.681(4) |

An embodiment of the invention is one, any or all of prior embodiments in this paragraph up through the first embodiment wherein the microporous crystalline zeolite is containing planar faults. An embodiment of the invention is one, any or all of prior embodiments in this paragraph up through the first embodiment wherein the planar faults are an offset of about ⅓ of a b axis of the microporous crystalline zeolite. An embodiment of the invention is one, any or all of prior embodiments in this paragraph up through the second embodiment wherein the microporous crystalline zeolite is represented by an empirical formula Mm$n+$RrAlxEySiOz where M represents hydrogen or a metal or metals selected from the group consisting of zinc, Group 1 (IUPAC 1) metals, Group 2 (IUPAC 2) metals, Group 3 (IUPAC 3) metals or lanthanide series metals of the periodic table, "m" is the mole ratio of M to Si and varies from 0 to about 1.0, "n" is the weighted average valence of M and has a value of about 1 to about 3, R is a structure directing agent or agents, "r" is the mole ratio of N from the organic structure directing agent or agents to Si and has a value of about 0 to about 1.0, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation z=(4+m+3●x+3●y)/2, and characterized in that it has the x-ray diffraction pattern having at least the d-spacings and intensities set forth in Table 1

TABLE 1

| 2θ | d (Å) | I/I$_0$ % |
|---|---|---|
| 7.16 | 12.34 | VW-W |
| 7.44 | 11.87 | VW-W |
| 8.58 | 10.30 | VW |
| 21.01* | 4.225 | VS |
| 22.07 | 4.024 | VW |
| 22.75 | 3.906 | MW-M |
| 24.19 | 3.676 | VW |
| 26.41 | 3.372 | VW-W |
| 32.73 | 2.734 | VW |
| 36.37 | 2.468 | VW |
| 44.01 | 2.056 | VW |

An embodiment of the invention is one, any or all of prior embodiments in this paragraph up through the first embodiment wherein microporous crystalline zeolite expressed by an empirical formula M$_m^{'N+}$Al$_x$E$_y$SiO$_z$ where M represents hydrogen or a metal or metals selected from the group consisting of zinc, Group 1 (IUPAC 1) metals, Group 2 (IUPAC 2) metals, Group 3 (IUPAC 3) metals or lanthanide series metals of the periodic table, "m'" is the mole ratio of M to Si and varies from 0 to about 1.0, "N" is the weighted average valence of M and has a value of about +1 to about +3, "X" is the mole ratio of Al to Si and has a value of from 0 to about 0.026, E is an element selected from the group consisting of gallium, iron, boron and mixtures thereof, "Y" is the mole ratio of E to Si and has a value from 0 to about 0.026, and "Z" is the mole ratio of O to (Al+E) and has a value determined by the equation z=(4+m+3●x+3●y)/2. An embodiment of the invention is one, any or all of prior embodiments in this paragraph up through the first embodiment wherein the microporous crystalline zeolite is characterized in that it has the x-ray diffraction pattern having at least the d-spacings and intensities set forth in Table 2.

TABLE 2

| 2θ | d (Å) | I/I$_0$ % |
|---|---|---|
| 7.19 | 12.28 | MW-S |
| 7.57 | 11.67 | W-M |
| 8.59 | 10.29 | W-MW |
| 14.72 | 6.013 | VW |
| 21.04* | 4.219 | VS |
| 22.15 | 4.010 | VW |
| 23.03 | 3.859 | MW-M |
| 24.34 | 3.654 | VW |
| 26.63 | 3.345 | VW-W |
| 36.47 | 2.462 | VW |
| 44.49 | 2.035 | VW |

A second embodiment of the invention is a process of preparing a microporous crystalline zeolite having a channel system comprising 10-membered rings of tetrahedrally coordinated atoms and 12-membered rings of tetrahedrally coordinated atoms in a single channel, the process comprising preparing a reaction mixture having a composition expressed in terms of mole ratios of the oxides of aM2O bR cAl2O3 eE2O3 SiO2 gH2O where M represents a metal or metals from hydrogen, zinc or Group 1 (IUPAC 1), Group 2 (IUPAC 2), Group 3 (IUPAC 3) or the lanthanide series of the periodic table, "a" has a value from 0 to about 0.5, R is an organic structure directing agent or agents, "b" has a value from about 0 to about 0.3, "c" has a value of from 0.0 to about 0.015, E is an element selected from the group consisting of gallium, iron, boron and mixtures thereof, "e" has a value from 0.0 to about 0.015,7 and "g" has a value from about 20 to about 40; reacting the reaction mixture at a temperature of about 150° to about 185° C. for a period of time of about 1 day to about 3 weeks under autogenous pressure until crystallization is complete; isolating a solid product; and washing the solid product with deionized water and drying the solid product. An embodiment of the invention is one, any or all of prior embodiments in this paragraph up through the second embodiment wherein second embodiment of the invention is a process of preparing the microporous crystalline zeolite comprising preparing a reaction mixture having a composition expressed in terms of mole ratios of the oxides of aM2O bR cAl2O3 eE2O3 SiO2 gH2O where M represents a metal or metals from hydrogen, zinc or Group 1 (IUPAC 1), Group 2 (IUPAC 2), Group 3 (IUPAC 3) or the lanthanide series of the periodic table, "a" has a value from 0 to about 0.5, R is an organic structure directing agent or agents, "b" has a value from about 0 to about 0.3, "c" has a value of from 0.0 to about 0.015, E is an element selected from the group consisting of gallium, iron, boron and mixtures thereof, "e" has a value from 0.0 to about 0.015,7 and "g" has a value from about 20 to about 40; reacting the reaction mixture at a temperature of about 150° to about 185° C. for a period of time of about 1 day to about 3 weeks under autogenous pressure until crystallization is complete; isolating a solid product; and washing the solid product with deionized water and drying the solid product. An embodiment of the invention is one, any or all of prior embodiments in this paragraph up through the second embodiment in this paragraph further comprising adding UZM-55 seeds to the reaction mixture. An embodiment of the invention is one, any or all of prior embodiments in this paragraph up through the second embodiment in this paragraph wherein a source for M is selected from the group consisting of sodium hydroxide, potassium hydroxide, sodium aluminate, potassium aluminate, sodium silicate, and potassium silicate. An embodiment of the invention is one, any or all of prior embodiments in this paragraph up through the second embodiment in this paragraph wherein a source for E is selected from the group consisting of alkali borates, boric acid, precipitated gallium oxyhydroxide, gallium sulfate, ferric sulfate, ferric chloride and mixtures thereof and a source for aluminum is selected from the group consisting of aluminum alkoxides, precipitated aluminas, aluminum metal, aluminum hydroxide, sodium aluminate, potassium aluminate, aluminum salts and alumina sols. An embodiment of the invention is one, any or all of prior embodiments in this paragraph up through the second embodiment in this paragraph wherein a source for silica is selected from the group consisting of tetraethylorthosilicate, colloidal silica, fumed silica, precipitated silica and alkali silicates. An embodiment of the invention is one, any or all of prior embodiments in this paragraph up through the second embodiment in this paragraph wherein R has a formula [bis-N,N'-diR1-(piperidinium)-R2]2+2X−, wherein R1 is selected from H or an alkyl group having a formula $C_qH_{2q+1}$, where q is in the range from 1 to 4, X is halide or hydroxide, the total number of C atoms in the formula is in a range of 11 to 24, and R2 is an alkyl group having the formula $C_pH_{2p}$, where p is in the range from 3 to 8 and is connected to the 1 and 1' N atoms at positions s and t of the alkyl chain where s and t are independently selected from 1 to p. An embodiment of the invention is one, any or all of prior embodiments in this paragraph up through the second embodiment in this paragraph further comprising modifying the microporous crystalline zeolite by one or more modifications selected from the group consisting of calcination, ion-exchange, steaming, acid extraction and ammonium hexafluorosilicate treatment.

A third embodiment of the invention is a hydrocarbon conversion process comprising contacting a hydrocarbon stream with a microporous crystalline zeolite having a channel system comprising 10-membered rings of tetrahedrally coordinated atoms and 12-membered rings of tetrahedrally coordinated atoms in a single channel wherein the contact is at conversion conditions to provide a converted hydrocarbon product comprising a hydrocarbon compound not present in the hydrocarbon stream.

The invention claimed is:

1. A microporous crystalline zeolite, UZM-55, having a channel system comprising 10-membered rings of tetrahedrally coordinated atoms and 12-membered rings of tetrahedrally coordinated atoms in a single channel, wherein the channel system is one-dimensional, and represented by an empirical formula:

$$M_m^{n+}R_rAl_xE_ySiO_z$$

where M represents hydrogen or a metal or metals selected from the group consisting of zinc, Group 1 (IUPAC 1) metals, Group 2 (IUPAC 2) metals, Group 3 (IUPAC 3) metals or lanthanide series metals of the periodic table, "m" is the mole ratio of M to Si and varies from 0 to about 1.0, "n" is the weighted average valence of M and has a value of about 1 to about 3, R is a structure directing agent or agents, "r" is the mole ratio of N from the organic structure directing agent or agents to Si and has a value of about 0 to about 1.0, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation:

and is characterized in that it has the x-ray diffraction pattern having at least the d-spacings and intensities set forth in Table 1:

TABLE 1

| 2θ | d (Å) | I/I₀ % |
|---|---|---|
| 7.16 | 12.34 | VW-W |
| 7.44 | 11.87 | VW-W |
| 8.58 | 10.30 | VW |
| 21.01* | 4.225 | VS |
| 22.07 | 4.024 | VW |
| 22.75 | 3.906 | MW-M |
| 24.19 | 3.676 | VW |
| 26.41 | 3.372 | VW-W |
| 32.73 | 2.734 | VW |
| 36.37 | 2.468 | VW |
| 44.01 | 2.056 | VW. |

2. The zeolite of claim 1 wherein the tetrahedrally coordinated atoms are Si, Al or E atoms and have atomic coordinates within ±0.75 Å as shown in Table 3

TABLE 3

| | Calcined, optimized | | |
|---|---|---|---|
| Site | X | Y | Z |
| T1 | 0.913(3) | 0.270(4) | 0.745(4) |
| T2 | 0.001(3) | 0.121(4) | 0.633(4) |
| T3 | 0.995(3) | 0.512(4) | 0.373(4) |
| T4 | 0.911(3) | 0.129(4) | 0.983(4) |
| T5 | 0.347(3) | 0.135(4) | 0.940(4) |
| T6 | 0.623(3) | 0.208(4) | 0.828(4) |
| T7 | 0.432(3) | 0.507(4) | 0.581(4) |
| T8 | 0.247(3) | 0.697(4) | 0.335(4) |
| T9 | 0.275(3) | 0.466(4) | 0.500(4) |
| T10 | 0.462(3) | 0.278(4) | 0.765(4) |
| T11 | 0.185(3) | 0.223(4) | 0.870(4) |
| T12 | 0.167(3) | 0.456(4) | 0.701(4) |
| T13 | 0.164(3) | 0.094(4) | 0.694(4) |
| T14 | 0.709(3) | 0.175(4) | 0.498(4) |
| T15 | 0.550(3) | 0.239(4) | 0.417(4) |
| T16 | 0.280(3) | 0.212(4) | 0.514(4) |
| T17 | 0.434(3) | 0.141(4) | 0.606(4) |
| T18 | 0.075(3) | 0.106(4) | 0.057(4) |
| T19 | 0.089(3) | 0.103(4) | 0.296(4) |
| T20 | 0.792(3) | 0.143(4) | 0.164(4) |
| T21 | 0.523(3) | 0.103(4) | 0.262(4) |
| T22 | 0.639(3) | 0.109(4) | 0.081(4) |
| T23 | 0.253(3) | 0.070(4) | 0.364(4) |
| T24 | 0.369(3) | 0.038(4) | 0.192(4) |
| T25 | 0.012(3) | 0.742(4) | 0.610(4) |
| T26 | 0.826(3) | 0.286(4) | 0.313(4) |
| T27 | 0.086(3) | 0.729(4) | 0.254(4) |
| T28 | 0.998(3) | 0.879(4) | 0.367(4) |
| T29 | 0.004(3) | 0.487(4) | 0.626(4) |
| T30 | 0.088(3) | 0.870(4) | 0.016(4) |
| T31 | 0.653(3) | 0.864(4) | 0.059(4) |
| T32 | 0.376(3) | 0.791(4) | 0.171(4) |
| T33 | 0.567(3) | 0.492(4) | 0.418(4) |
| T34 | 0.752(3) | 0.302(4) | 0.664(4) |
| T35 | 0.724(3) | 0.534(4) | 0.499(4) |
| T36 | 0.537(3) | 0.721(4) | 0.234(4) |
| T37 | 0.814(3) | 0.776(4) | 0.129(4) |
| T38 | 0.832(3) | 0.543(4) | 0.299(4) |
| T39 | 0.835(3) | 0.905(4) | 0.305(4) |
| T40 | 0.290(3) | 0.824(4) | 0.501(4) |
| T41 | 0.449(3) | 0.760(4) | 0.582(4) |
| T42 | 0.719(3) | 0.787(4) | 0.485(4) |
| T43 | 0.565(3) | 0.858(4) | 0.393(4) |
| T44 | 0.924(3) | 0.893(4) | 0.942(4) |
| T45 | 0.910(3) | 0.896(4) | 0.704(4) |
| T46 | 0.207(3) | 0.856(4) | 0.835(4) |
| T47 | 0.476(3) | 0.896(4) | 0.737(4) |
| T48 | 0.360(3) | 0.890(4) | 0.918(4) |
| T49 | 0.746(3) | 0.929(4) | 0.635(4) |

TABLE 3-continued

Calcined, optimized

| Site | X | Y | Z |
| --- | --- | --- | --- |
| T50 | 0.630(3) | 0.961(4) | 0.807(4) |
| T51 | 0.987(3) | 0.257(4) | 0.389(4) |
| T52 | 0.173(3) | 0.713(4) | 0.686(4). |

3. The zeolite of claim 1 wherein the tetrahedrally coordinated atoms are Si, Al or E atoms and have atomic coordinates within ±0.75 Å as shown in Table 4

TABLE 4

Rietveld refinement results

| Site | X | Y | Z |
| --- | --- | --- | --- |
| T1 | 0.906(3) | 0.259(4) | 0.751(4) |
| T2 | 0.093(3) | 0.740(4) | 0.248(4) |
| T3 | 0.018(3) | 0.119(4) | 0.648(4) |
| T4 | 0.981(3) | 0.880(4) | 0.351(4) |
| T5 | 0.005(3) | 0.504(4) | 0.376(4) |
| T6 | 0.994(3) | 0.495(4) | 0.623(4) |
| T7 | 0.907(3) | 0.123(4) | 0.984(4) |
| T8 | 0.092(3) | 0.876(4) | 0.015(4) |
| T9 | 0.337(3) | 0.141(4) | 0.932(4) |
| T10 | 0.662(3) | 0.858(4) | 0.067(4) |
| T11 | 0.639(3) | 0.204(4) | 0.804(4) |
| T12 | 0.360(3) | 0.795(4) | 0.195(4) |
| T13 | 0.431(3) | 0.510(4) | 0.579(4) |
| T14 | 0.568(3) | 0.489(4) | 0.420(4) |
| T15 | 0.239(3) | 0.709(4) | 0.355(4) |
| T16 | 0.760(3) | 0.290(4) | 0.645(4) |
| T17 | 0.275(3) | 0.479(4) | 0.494(4) |
| T18 | 0.724(3) | 0.520(4) | 0.505(4) |
| T19 | 0.464(3) | 0.267(4) | 0.741(4) |
| T20 | 0.535(3) | 0.732(4) | 0.258(4) |
| T21 | 0.199(3) | 0.233(4) | 0.855(4) |
| T22 | 0.800(3) | 0.767(4) | 0.144(4) |
| T23 | 0.166(3) | 0.467(4) | 0.691(4) |
| T24 | 0.833(3) | 0.532(4) | 0.308(4) |
| T25 | 0.179(3) | 0.096(4) | 0.694(4) |
| T26 | 0.820(3) | 0.903(4) | 0.305(4) |
| T27 | 0.725(3) | 0.149(4) | 0.485(4) |
| T28 | 0.274(3) | 0.851(4) | 0.514(4) |
| T29 | 0.565(3) | 0.218(4) | 0.417(4) |
| T30 | 0.434(3) | 0.781(4) | 0.582(4) |
| T31 | 0.273(3) | 0.204(4) | 0.506(4) |
| T32 | 0.726(3) | 0.795(4) | 0.493(4) |
| T33 | 0.433(3) | 0.136(4) | 0.586(4) |
| T34 | 0.566(3) | 0.863(4) | 0.413(4) |
| T35 | 0.068(3) | 0.138(4) | 0.010(4) |
| T36 | 0.931(3) | 0.861(4) | 0.989(4) |
| T37 | 0.074(3) | 0.093(4) | 0.277(4) |
| T38 | 0.925(3) | 0.906(4) | 0.722(4) |
| T39 | 0.801(3) | 0.139(4) | 0.175(4) |
| T40 | 0.198(3) | 0.860(4) | 0.824(4) |
| T41 | 0.537(3) | 0.098(4) | 0.235(4) |
| T42 | 0.462(3) | 0.902(4) | 0.764(4) |
| T43 | 0.653(3) | 0.113(4) | 0.068(4) |
| T44 | 0.346(3) | 0.886(4) | 0.931(4) |
| T45 | 0.241(3) | 0.072(4) | 0.356(4) |
| T46 | 0.758(3) | 0.927(4) | 0.643(4) |
| T47 | 0.370(3) | 0.057(4) | 0.182(4) |
| T48 | 0.629(3) | 0.942(4) | 0.817(4) |
| T49 | 0.002(3) | 0.761(4) | 0.593(4) |
| T50 | 0.997(3) | 0.238(4) | 0.406(4) |
| T51 | 0.833(3) | 0.267(4) | 0.318(4) |
| T52 | 0.166(3) | 0.732(4) | 0.681(4). |

4. The microporous crystalline zeolite of claim 1 comprising a framework of tetrahedral atoms bridged by oxygen atoms, the tetrahedral framework being defined by a unit cell of a=17.80 Å, b=12.23 Å, c=12.93 Å, alpha=71.79°, beta=88.16°, gamma=90.25° with fractional atomic coordinates shown in Table 3 or Table 4 wherein each cell axis length may vary within +/−0.75 Å, each cell angle may vary within 1.0° and each t-site position may vary within about +/−0.5 Å wherein Tables 3 and 4 is as follows:

TABLE 3

Calcined, optimized

| Site | X | Y | Z |
| --- | --- | --- | --- |
| T1 | 0.913(3) | 0.270(4) | 0.745(4) |
| T2 | 0.001(3) | 0.121(4) | 0.633(4) |
| T3 | 0.995(3) | 0.512(4) | 0.373(4) |
| T4 | 0.911(3) | 0.129(4) | 0.983(4) |
| T5 | 0.347(3) | 0.135(4) | 0.940(4) |
| T6 | 0.623(3) | 0.208(4) | 0.828(4) |
| T7 | 0.432(3) | 0.507(4) | 0.581(4) |
| T8 | 0.247(3) | 0.697(4) | 0.335(4) |
| T9 | 0.275(3) | 0.466(4) | 0.500(4) |
| T10 | 0.462(3) | 0.278(4) | 0.765(4) |
| T11 | 0.185(3) | 0.223(4) | 0.870(4) |
| T12 | 0.167(3) | 0.456(4) | 0.701(4) |
| T13 | 0.164(3) | 0.094(4) | 0.694(4) |
| T14 | 0.709(3) | 0.175(4) | 0.498(4) |
| T15 | 0.550(3) | 0.239(4) | 0.417(4) |
| T16 | 0.280(3) | 0.212(4) | 0.514(4) |
| T17 | 0.434(3) | 0.141(4) | 0.606(4) |
| T18 | 0.075(3) | 0.106(4) | 0.057(4) |
| T19 | 0.089(3) | 0.103(4) | 0.296(4) |
| T20 | 0.792(3) | 0.143(4) | 0.164(4) |
| T21 | 0.523(3) | 0.103(4) | 0.262(4) |
| T22 | 0.639(3) | 0.109(4) | 0.081(4) |
| T23 | 0.253(3) | 0.070(4) | 0.364(4) |
| T24 | 0.369(3) | 0.038(4) | 0.192(4) |
| T25 | 0.012(3) | 0.742(4) | 0.610(4) |
| T26 | 0.826(3) | 0.286(4) | 0.313(4) |
| T27 | 0.086(3) | 0.729(4) | 0.254(4) |
| T28 | 0.998(3) | 0.879(4) | 0.367(4) |
| T29 | 0.004(3) | 0.487(4) | 0.626(4) |
| T30 | 0.088(3) | 0.870(4) | 0.016(4) |
| T31 | 0.653(3) | 0.864(4) | 0.059(4) |
| T32 | 0.376(3) | 0.791(4) | 0.171(4) |
| T33 | 0.567(3) | 0.492(4) | 0.418(4) |
| T34 | 0.752(3) | 0.302(4) | 0.664(4) |
| T35 | 0.724(3) | 0.534(4) | 0.499(4) |
| T36 | 0.537(3) | 0.721(4) | 0.234(4) |
| T37 | 0.814(3) | 0.776(4) | 0.129(4) |
| T38 | 0.832(3) | 0.543(4) | 0.299(4) |
| T39 | 0.835(3) | 0.905(4) | 0.305(4) |
| T40 | 0.290(3) | 0.824(4) | 0.501(4) |
| T41 | 0.449(3) | 0.760(4) | 0.582(4) |
| T42 | 0.719(3) | 0.787(4) | 0.485(4) |
| T43 | 0.565(3) | 0.858(4) | 0.393(4) |
| T44 | 0.924(3) | 0.893(4) | 0.942(4) |
| T45 | 0.910(3) | 0.896(4) | 0.704(4) |
| T46 | 0.207(3) | 0.856(4) | 0.835(4) |
| T47 | 0.476(3) | 0.896(4) | 0.737(4) |
| T48 | 0.360(3) | 0.890(4) | 0.918(4) |
| T49 | 0.746(3) | 0.929(4) | 0.635(4) |
| T50 | 0.630(3) | 0.961(4) | 0.807(4) |
| T51 | 0.987(3) | 0.257(4) | 0.389(4) |
| T52 | 0.173(3) | 0.713(4) | 0.686(4) |

TABLE 4

Rietveld refinement results

| Site | X | Y | Z |
| --- | --- | --- | --- |
| T1 | 0.906(3) | 0.259(4) | 0.751(4) |
| T2 | 0.093(3) | 0.740(4) | 0.248(4) |
| T3 | 0.018(3) | 0.119(4) | 0.648(4) |
| T4 | 0.981(3) | 0.880(4) | 0.351(4) |
| T5 | 0.005(3) | 0.504(4) | 0.376(4) |
| T6 | 0.994(3) | 0.495(4) | 0.623(4) |
| T7 | 0.907(3) | 0.123(4) | 0.984(4) |
| T8 | 0.092(3) | 0.876(4) | 0.015(4) |
| T9 | 0.337(3) | 0.141(4) | 0.932(4) |
| T10 | 0.662(3) | 0.858(4) | 0.067(4) |

TABLE 4-continued

Rietveld refinement results

| Site | X | Y | Z |
|---|---|---|---|
| T11 | 0.639(3) | 0.204(4) | 0.804(4) |
| T12 | 0.360(3) | 0.795(4) | 0.195(4) |
| T13 | 0.431(3) | 0.510(4) | 0.579(4) |
| T14 | 0.568(3) | 0.489(4) | 0.420(4) |
| T15 | 0.239(3) | 0.709(4) | 0.355(4) |
| T16 | 0.760(3) | 0.290(4) | 0.645(4) |
| T17 | 0.275(3) | 0.479(4) | 0.494(4) |
| T18 | 0.724(3) | 0.520(4) | 0.505(4) |
| T19 | 0.464(3) | 0.267(4) | 0.741(4) |
| T20 | 0.535(3) | 0.732(4) | 0.258(4) |
| T21 | 0.199(3) | 0.233(4) | 0.855(4) |
| T22 | 0.800(3) | 0.767(4) | 0.144(4) |
| T23 | 0.166(3) | 0.467(4) | 0.691(4) |
| T24 | 0.833(3) | 0.532(4) | 0.308(4) |
| T25 | 0.179(3) | 0.096(4) | 0.694(4) |
| T26 | 0.820(3) | 0.903(4) | 0.305(4) |
| T27 | 0.725(3) | 0.149(4) | 0.485(4) |
| T28 | 0.274(3) | 0.851(4) | 0.514(4) |
| T29 | 0.565(3) | 0.218(4) | 0.417(4) |
| T30 | 0.434(3) | 0.781(4) | 0.582(4) |
| T31 | 0.273(3) | 0.204(4) | 0.506(4) |
| T32 | 0.726(3) | 0.795(4) | 0.493(4) |
| T33 | 0.433(3) | 0.136(4) | 0.586(4) |
| T34 | 0.566(3) | 0.863(4) | 0.413(4) |
| T35 | 0.068(3) | 0.138(4) | 0.010(4) |
| T36 | 0.931(3) | 0.861(4) | 0.989(4) |
| T37 | 0.074(3) | 0.093(4) | 0.277(4) |
| T38 | 0.925(3) | 0.906(4) | 0.722(4) |
| T39 | 0.801(3) | 0.139(4) | 0.175(4) |
| T40 | 0.198(3) | 0.860(4) | 0.824(4) |
| T41 | 0.537(3) | 0.098(4) | 0.235(4) |
| T42 | 0.462(3) | 0.902(4) | 0.764(4) |
| T43 | 0.653(3) | 0.113(4) | 0.068(4) |
| T44 | 0.346(3) | 0.886(4) | 0.931(4) |
| T45 | 0.241(3) | 0.072(4) | 0.356(4) |
| T46 | 0.758(3) | 0.927(4) | 0.643(4) |
| T47 | 0.370(3) | 0.057(4) | 0.182(4) |
| T48 | 0.629(3) | 0.942(4) | 0.817(4) |
| T49 | 0.002(3) | 0.761(4) | 0.593(4) |
| T50 | 0.997(3) | 0.238(4) | 0.406(4) |
| T51 | 0.833(3) | 0.267(4) | 0.318(4) |
| T52 | 0.166(3) | 0.732(4) | 0.681(4). |

5. The microporous crystalline zeolite of claim 1 containing planar faults.

6. The microporous crystalline zeolite of claim 5 wherein the planar faults are an offset of about ⅓ of a b axis of said microporous crystalline zeolite.

7. The microporous crystalline zeolite of claim 1 that in a calcined form is characterized in that it has the x-ray diffraction pattern having at least the d-spacings and intensities set forth in Table 2

TABLE 2

| 2θ | d (Å) | I/I₀ % |
|---|---|---|
| 7.19 | 12.28 | MW-S |
| 7.57 | 11.67 | W-M |
| 8.59 | 10.29 | W-MW |
| 14.72 | 6.013 | VW |
| 21.04* | 4.219 | VS |
| 22.15 | 4.010 | VW |
| 23.03 | 3.859 | MW-M |
| 24.34 | 3.654 | VW |
| 26.63 | 3.345 | VW-W |
| 36.47 | 2.462 | VW |
| 44.49 | 2.035 | VW. |

8. A method of preparing a microporous crystalline zeolite, UZM-55, having a channel system comprising 10-membered rings of tetrahedrally coordinated atoms and 12-membered rings of tetrahedrally coordinated atoms in a single channel, wherein the channel system is one-dimensional, and represented by an empirical formula:

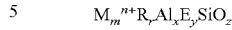

where M represents hydrogen or a metal or metals selected from the group consisting of zinc, Group 1 (IUPAC 1) metals, Group 2 (IUPAC 2) metals, Group 3 (IUPAC 3) metals or lanthanide series metals of the periodic table, "m" is the mole ratio of M to Si and varies from about 0 to about 1.0, "n" is the weighted average valence of M and has a value of about 1 to about 3, R is a structure directing agent or agents, "r" is the mole ratio of N from the organic structure directing agent or agents to Si and has a value of about 0 to about 1.0, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation:

$$z=(4+m\cdot n+3\cdot x+3\cdot y)/2$$

and is characterized in that it has the x-ray diffraction pattern having at least the d-spacings and intensities set forth in Table 1:

TABLE 1

| 2θ | d(Å) | I/I₀ % |
|---|---|---|
| 7.16 | 12.34 | VW-W |
| 7.44 | 11.87 | VW-W |
| 8.58 | 10.30 | VW |
| 21.01* | 4.225 | VS |
| 22.07 | 4.024 | VW |
| 22.75 | 3.906 | MW-M |
| 24.19 | 3.676 | VW |
| 26.41 | 3.372 | VW-W |
| 32.73 | 2.734 | VW |
| 36.37 | 2.468 | VW |
| 44.01 | 2.056 | VW | the process comprising:
preparing a reaction mixture having composition expressed in terms of mole ratios of the oxides of

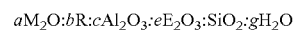

where M represents a metal or metals from hydrogen, zinc or Group 1 (IUPAC 1), Group 2 (IUPAC 2), Group 3 (IUPAC 3) or the lanthanide series of the periodic table, "a" has a value from 0 to about 0.5,
R is an organic structure directing agent or agents wherein R has a formula [bis-N,N'-diR₁-(piperidinium)-R₂]²⁺2X⁻, R₁ is selected from H or an alkyl group having a formula $C_qH_{2q+1}$, where q is in the range from 1 to 4, X is halide or hydroxide, the total number of C atoms in the formula is in a range of 11 to 24, and R₂ is an alkyl group having the formula $C_pH_{2p}$, where p is equal to 6 and is connected to the 1 and 1' N atoms at positions s and t of the alkyl chain where s and t are independently selected from 1 to p,
and where the source of R is a pre-reacted aqueous solution wherein pre-reaction comprises preparing an aqueous mixture comprising water, a substituted hydrocarbon and an amine; reacting the aqueous mixture; obtaining a solution comprising the organoammonium compound; and wherein the mixture and the solution are essentially free of aluminum and silicon, where the pre-reaction temperature is from about 20° C. to about 100° C., and for a time from about 0.5 hours to about 48 hours, "b" has a value from about 0 to about 0.3, "c" has a value of from 0.0 to about 0.015, E is an element selected from the group consisting of gallium, iron, boron and mixtures thereof, "e" has a value from 0.0 to about 0.015,7 and "g" has a value from about 20 to about 40;

reacting the reaction mixture at a temperature of about 150° to about 185° C. for a period of time of about 1 day to about 3 weeks under autogenous pressure until crystallization is complete;

isolating a solid product; and washing the solid product with deionized water and drying the solid product.

9. The method of claim 8 further comprising adding UZM-55 seeds to the reaction mixture.

10. The method of claim 8 wherein a source for M is selected from the group consisting of sodium hydroxide, potassium hydroxide, sodium aluminate, potassium aluminate, sodium silicate, and potassium silicate.

11. The method of claim 8 wherein a source for E is selected from the group consisting of alkali borates, boric acid, precipitated gallium oxyhydroxide, gallium sulfate, ferric sulfate, ferric chloride and mixtures thereof and a source for aluminum is selected from the group consisting of aluminum alkoxides, precipitated aluminas, aluminum metal, aluminum hydroxide, sodium aluminate, potassium aluminate, aluminum salts and alumina sols.

12. The method of claim 8 wherein a source for silica is selected from the group consisting of tetraethylorthosilicate, colloidal silica, fumed silica, precipitated silica and alkali silicates.

13. The method of claim 8 further comprising modifying said microporous crystalline zeolite by one or more modifications selected from the group consisting of calcination, ion-exchange, steaming, acid extraction and ammonium hexafluorosilicate treatment.

14. A hydrocarbon conversion process comprising contacting the hydrocarbon with a microporous crystalline zeolite, UZM-55, having a channel system comprising 10-membered rings of tetrahedrally coordinated atoms and 12-membered rings of tetrahedrally coordinated atoms in a single channel and represented by an empirical formula:

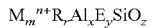

where M represents hydrogen or a metal or metals selected from the group consisting of zinc, Group 1 (IUPAC 1) metals, Group 2 (IUPAC 2) metals, Group 3 (IUPAC 3) metals or lanthanide series metals of the periodic table, "m" is the mole ratio of M to Si and varies from 0 to about 1.0, "n" is the weighted average valence of M and has a value of about 1 to about 3, R is a structure directing agent or agents, "r" is the mole ratio of N from the organic structure directing agent or agents to Si and has a value of about 0 to about 1.0, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation:

$$z=(4+m+3\bullet x+3\bullet y)/2$$

and is characterized in that it has the x-ray diffraction pattern having at least the d-spacings and intensities set forth in Table 1:

TABLE 1

| 2θ | d(Å) | I/I₀ % |
|---|---|---|
| 7.16 | 12.34 | VW-W |
| 7.44 | 11.87 | VW-W |
| 8.58 | 10.30 | VW |
| 21.01* | 4.225 | VS |
| 22.07 | 4.024 | VW |
| 22.75 | 3.906 | MW-M |
| 24.19 | 3.676 | VW |
| 26.41 | 3.372 | VW-W |
| 32.73 | 2.734 | VW |
| 36.37 | 2.468 | VW |
| 44.01 | 2.056 | VW | wherein said contact is at conversion conditions to provide a converted hydrocarbon product wherein the hydrocarbon conversion process is selected from the group consisting of conversion of methanol to olefins, ethylene to propylene, oligomerization, isomerization of paraffins, paraffin cracking, xylene isomerization, toluene disproportionation, ring opening and cracking to remove benzene co-boilers and alkylation of aromatics with paraffins.

* * * * *